US009730987B2

(12) United States Patent
Detraz et al.

(10) Patent No.: US 9,730,987 B2
(45) **Date of Patent: *Aug. 15, 2017**

(54) VACCINE FORMULATIONS COMPRISING SAPONIN-CONTAINING ADJUVANTS

(71) Applicant: MERIAL INC., Duluth, GA (US)

(72) Inventors: Noel Joseph Francois Detraz, Lyons (FR); Guillaume Rigaut, Lyons (FR)

(73) Assignee: MERIAL INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/632,863

(22) Filed: Feb. 26, 2015

(65) Prior Publication Data

US 2015/0196487 A1 Jul. 16, 2015

Related U.S. Application Data

(63) Continuation of application No. 12/878,630, filed on Sep. 9, 2010, now Pat. No. 9,107,859.

(60) Provisional application No. 61/241,171, filed on Sep. 10, 2009.

(51) Int. Cl.

| | |
|---|---|
| ***A61K 39/00*** | (2006.01) |
| ***A61K 47/26*** | (2006.01) |
| ***A61K 9/00*** | (2006.01) |
| ***A61K 9/107*** | (2006.01) |
| ***A61K 45/06*** | (2006.01) |
| ***A61K 47/06*** | (2006.01) |
| ***C12N 7/00*** | (2006.01) |
| ***A61K 39/39*** | (2006.01) |
| ***A61K 39/02*** | (2006.01) |
| ***A61K 39/12*** | (2006.01) |
| ***A61K 39/135*** | (2006.01) |
| ***A61K 39/125*** | (2006.01) |

(52) U.S. Cl.

CPC ............ *A61K 39/00* (2013.01); *A61K 9/0019* (2013.01); *A61K 9/107* (2013.01); *A61K 39/0241* (2013.01); *A61K 39/12* (2013.01); *A61K 39/135* (2013.01); *A61K 39/39* (2013.01); *A61K 45/06* (2013.01); *A61K 47/06* (2013.01); *A61K 47/26* (2013.01); *C12N 7/00* (2013.01); *A61K 39/125* (2013.01); *A61K 2039/52* (2013.01); *A61K 2039/525* (2013.01); *A61K 2039/5252* (2013.01); *A61K 2039/54* (2013.01); *A61K 2039/552* (2013.01); *A61K 2039/55505* (2013.01); *A61K 2039/55566* (2013.01); *A61K 2039/55577* (2013.01); *C12N 2750/00022* (2013.01); *C12N 2750/00034* (2013.01); *C12N 2750/10034* (2013.01); *C12N 2770/32022* (2013.01); *C12N 2770/32134* (2013.01)

(58) Field of Classification Search

CPC ................ A61K 39/12; A61K 2300/00; A61K 2039/552; A61K 2039/5254; A61K 2039/55566; A61K 2039/53; A61K 2039/5252; A61K 39/135; A61K 2039/525; A61K 2039/55577; C12N 7/00; C12N 2750/10022; C12N 2750/10021; C12N 2750/10051; C12N 2750/00021

See application file for complete search history.

(56) References Cited

PUBLICATIONS

Doel TR. FMD vaccines. Virus Res. Jan. 2003;91(1):81-99.*

Advisory Action. U.S. Appl. No. 12/878,630, mailed Mar. 19, 2015.*

Claims. U.S. Appl. No. 12/878,630, presented Mar. 26, 2015.*

37 CFR 1.132 Declaration. U.S. Appl. No. 12/878,630, presented Apr. 1, 2015.*

Pre-appeals conference decision. U.S. Appl. No. 12/878,630, mailed Feb. 19, 2015.*

Notice of Allowance. U.S. Appl. No. 12/878,630 mailed Apr. 9, 2015.*

* cited by examiner

*Primary Examiner* — Rachel B Gill

(74) *Attorney, Agent, or Firm* — Judy Jarecki-Black; Chad Kitchen; Merial Inc.

(57) ABSTRACT

The present invention provides for a novel oil-in-water (O/W) emulsion, with increased stability in the presence of bacterial or viral suspensions, especially those concentrated and non-purified (crude extracts) or minimally purified. The emulsion of the present invention can act as vehicle for the delivery of a pharmaceutical composition comprising at least one immunogen and, in particular, an immunogen selected from the group consisting of an inactivated pathogen, an attenuated pathogen, a subunit, a recombinant expression vector, and a plasmid or combinations thereof.

15 Claims, 10 Drawing Sheets

Phase Inversion Temperature (PIT) Determination by Conductivity – Trial 1

Phase Inversion Temperature (PIT) Determination by Conductivity – Trial 2

VACCINE FORMULATIONS COMPRISING SAPONIN-CONTAINING ADJUVANTS

INCORPORATION BY REFERENCE

This application is a continuation of and claims priority to U.S. application Ser. No. 12/878,630, filed on Sep. 9, 2010, which claims priority to U.S. provisional patent application No. 61/241,171, filed on Sep. 10, 2009, and further makes reference to the following patent applications: U.S. patent application Ser. No. 12/027,776, filed on Feb. 7, 2008, U.S. patent application Ser. No. 10/899,181, filed on Jul. 26, 2004, now granted as U.S. Pat. No. 7,371,395, and U.S. provisional patent application No. 60/490,345, filed on Jul. 24, 2003. The foregoing applications, and all documents cited therein or during their prosecution ("applicant cited documents") and all documents cited or referenced in the applicant cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to oil-in-water emulsions, their use as adjuvants, and pharmaceutical, immunologic, or vaccine compositions comprising the same.

BACKGROUND

The use of adjuvants in vaccines is well known. An adjuvant is a compound that, when combined with a vaccine antigen, increases the immune response to the vaccine antigen as compared to the response induced by the vaccine antigen alone. Among strategies that promote antigen immunogenicity are those that render vaccine antigens particulate, those that polymerize or emulsify vaccine antigens, methods of encapsulating vaccine antigens, ways of increasing host innate cytokine responses, and methods that target vaccine antigens to antigen presenting cells (Nossal, 1999, In: *Fundamental Immunology*. Paul (Ed.), Lippincott-Raven Publishers, Philadelphia, Pa.; Vogel and Powell, 1995, In: *Vaccine Design*. The Subunit and Adjuvant Approach. Powell and Newman (Eds.), Plenum Press, NY, N.Y. p. 141). Because of the essential role adjuvants play in improving the immunogenicity of vaccine antigens, the use of adjuvants in the formulation of vaccines has been virtually ubiquitous (Nossal, 1999, supra; Vogel and Powell, 1995, supra; see also PCT publication WO 97/18837, the teachings of which are incorporated herein by reference). Conventional adjuvants, well-known in the art, are diverse in nature. They may, for example, consist of water-insoluble inorganic salts, liposomes, micelles or emulsions, i.e. Freund's adjuvant. Other adjuvants may be found in Vogel and Powell, 1995, mentioned supra. Although there is no single mechanism of adjuvant action, an essential characteristic is their ability to significantly increase the immune response to a vaccine antigen as compared to the response induced by the vaccine antigen alone (Nossal, 1999, supra; Vogel and Powell, 1995, supra). In this regard, some adjuvants are more effective at augmenting humoral immune responses; other adjuvants are more effective at increasing cell-mediated immune responses (Vogel and Powell, 1995, supra); and yet another group of adjuvants increase both humoral and cell-mediated immune responses against vaccine antigens (Vogel and Powell, 1995, supra).

Generally, emulsions used in vaccine formulation comprise a mixture of oil, aqueous solution and surfactants. Some emulsions incorporate a lipophilic surfactant such as SPAN 80® and a hydrophilic surfactant such as TWEEN 80®.

However, problems of stability can be observed with emulsions used as vaccine adjuvants, in particular during storage or transport. This is particularly true when these compositions contain concentrated immunogens, especially non-purified concentrated immunogens. Typically, this is the case with adjuvants used in inactivated (killed) vaccines. This problem is even more significant with multivalent vaccine compositions because the immunogens are more concentrated in the same volume of diluent.

Another problem with adjuvant use is linked to a risk of adverse events such as toxicity or local inflammation at the site of injection. For example, a local inflammatory response and/or granulomae may result after injection. In order to limit such an adverse reaction, surfactants and other components in the emulsion may be reduced; however, the reduction may then result in a decrease in the stability of the vaccine composition. There is, therefore, a need for novel adjuvants and vaccine compositions containing such adjuvants with increased safety and stability.

SUMMARY OF THE INVENTION

In a first embodiment the present invention provides for a novel oil-in-water (O/W) emulsion, with increased stability in the presence of bacterial or viral suspensions, especially those concentrated and non-purified or weakly purified.

Another embodiment of the present invention provides for a stable, safe and easily administrable, in particular injectable, O/W emulsion acting as a vehicle for the delivery of a pharmaceutical composition comprising at least one active ingredient that may be, more particularly, an immunogen.

Yet another embodiment of the present invention provides for a stable, safe and injectable O/W emulsion acting as an adjuvant to increase the immune response induced by an immunogen. In particular, the present invention provides a novel adjuvant which, when used in a vaccine composition containing an immunogen increases the vaccinate's cellular immune response, humoral immune response or, preferably, both to the immunogen.

Yet another embodiment of the present invention provides a stable, safe and immunogenic composition or vaccine comprising an O/W emulsion.

A further embodiment of the present invention provides for a method of making a vaccine composition using the adjuvant of the instant invention; the vaccine composition so obtained; and methods of using thereof.

Still another embodiment of the present invention provides for a kit comprising one or more vials. In one embodiment, the kit comprises one vial containing the adjuvant of the present invention and an immunogen or other pharmaceutical product. In yet another embodiment, the kit comprises an immunogen or other pharmaceutical product in a first vial, and an adjuvant made according to the present invention in a second vial, with the adjuvant designed to be mixed with the immunogen or other vaccine product before use.

In one embodiment, the present invention provides for an injectable oil-in-water (O/W) emulsion comprising:

(1) an aqueous solution comprising an immunogen;

(2) an aqueous solution comprising a hydrophilic ionic surfactant such as saponin (3) an optional aqueous solution comprising aluminum hydroxide (4) a mineral oil;

(5) a non-ionic lipophilic surfactant;

(6) a non-ionic hydrophilic surfactant having a low HLB value which comprises ethoxylated fatty acid diesters of sorbitan (generally having HLB value between 11 and 13).

In another embodiment, the present invention provides for an injectable oil-in-water (O/W) emulsion comprising:

(1) an aqueous solution comprising an immunogen;

(2) an aqueous solution comprising a hydrophilic ionic surfactant such as saponin (3) a mineral oil;

(4) a non-ionic lipophilic surfactant;

(5) a non-ionic hydrophilic surfactant having a low HLB value which comprises ethoxylated fatty acid diesters of sorbitan (generally having HLB value between 11 and 13).

In another embodiment, the present invention provides for an injectable oil-in-water (O/W) emulsion comprising:

(1) an aqueous solution comprising an immunogen;

(2) an aqueous solution comprising a hydrophilic ionic surfactant such as saponin (3) an optional aqueous solution comprising aluminum hydroxide (4) a non-ionic hydrophilic surfactant having a high hydrophilic-lipophilic balance (HLB) value greater than 13 and less than 40, in particular HLB≥13.5, and preferably HLB≥14;

(5) a mineral oil;

(6) a non-ionic lipophilic surfactant;

(7) a non-ionic hydrophilic surfactant having a low HLB value (HLB value of about 9 to about 13).

In another embodiment, the present invention provides for an injectable oil-in-water (O/W) emulsion comprising:

(1) an aqueous solution comprising an immunogen;

(2) an aqueous solution comprising a hydrophilic ionic surfactant such as saponin (3) a non-ionic hydrophilic surfactant having a high hydrophilic-lipophilic balance (HLB) value greater than 13 and less than 40, in particular HLB≥13.5, and preferably HLB≥14;

(4) a mineral oil;

(5) a non-ionic lipophilic surfactant;

(6) a non-ionic hydrophilic surfactant having a low HLB value (HLB value of about 9 to about 13).

In yet another embodiment, the present invention provides for a vaccine composition comprising a novel emulsion containing at least one immunogen suitable for eliciting an immunologic response in a vaccinate. The invention further provides such compositions wherein the emulsion acts as an adjuvant to increase the immune response induced by the immunogen, in particular, to increase the cellular response, the humoral response or preferably both.

In another embodiment the present invention provides for a method of making a vaccine composition wherein an immunogen, especially an immunogen in dry form, which can be obtained, for example, by lyophilization or by vitrification, or in an aqueous solution, especially wherein said dry form or said aqueous solution additionally comprises an ionic surfactant, for example saponin, and optionally additionally comprises aluminum hydroxide, is mixed with the adjuvant according to the instant invention. The immunogen may be selected from the group consisting of: inactivated pathogens, attenuated pathogens, sub-unit antigens, purified antigens, unpurified antigens, or antigens produced recombinantly using bacterial, yeast, plant, insect, or animal cells, expression vectors including plasmids, and the like. The antigens may be purified by means well-known in the art including, but not limited to, ultrafiltration, ultracentrifugation, size-exclusion gel-filtration, ion-exchange chromatography, and PEG-purification. The pathogen may be bacterial, viral, protozoal, or fungal in origin or the immunogen may constitute an antitoxin.

In another embodiment, the present invention provides for a method of inducing an immune response in a vaccinate against a pathogen comprising administering the vaccine composition of the present invention to the vaccinate.

In another embodiment, the present invention provides for kits comprising a single vial containing purified immunogens and the emulsion according to the instant invention. In one such embodiment, the immunogens contained within the single vial comprise purified FMD virus antigens.

In another embodiment, the present invention provides for kits comprising at least two vials, in a first vial an immunogen, especially an immunogen in dry form or in solution in an aqueous medium, especially wherein said dry form or said aqueous solution additionally comprises an ionic surfactant, advantageously saponin, and optionally additionally comprises aluminum hydroxide, and in a second vial an adjuvant or emulsion according to the present invention. The use of kits that comprise at least two vials is particularly effective in cases where the combination of the discrete components (i.e. the mixture into a single vial of the contents of the at least two vials) would result in a vaccine formulation of reduced stability.

It is noted that in this disclosure and particularly in the claims, terms such as "comprises", "comprised", "comprising" and the like can have the meaning attributed to such terms in U.S. Patent law; e.g., they can mean "includes", "included", "including", and the like; and that terms such as "consisting essentially of" and "consists essentially of" have the meaning ascribed to them by U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein.

DETAILED DESCRIPTION OF THE INVENTION

Figure 1:
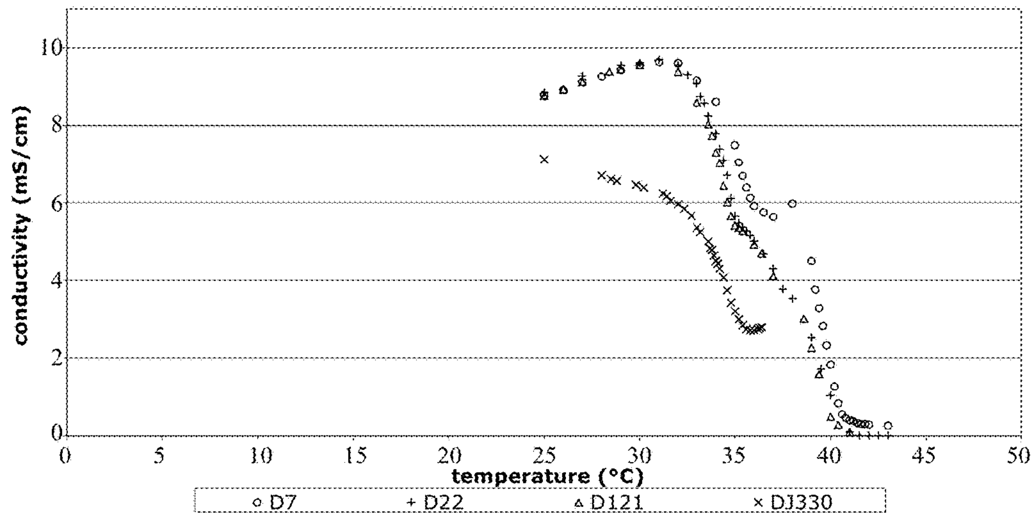
FIG. 1 provides graphs of the Phase Inversion Temperature (PIT) determination (measured by conductivity) for the vaccine formulations of trials 1 & 2 on days 7, 22, 121, and 330 (one year stability study). The PIT determination is one measure of vaccine formulation stability.
Figure 1:
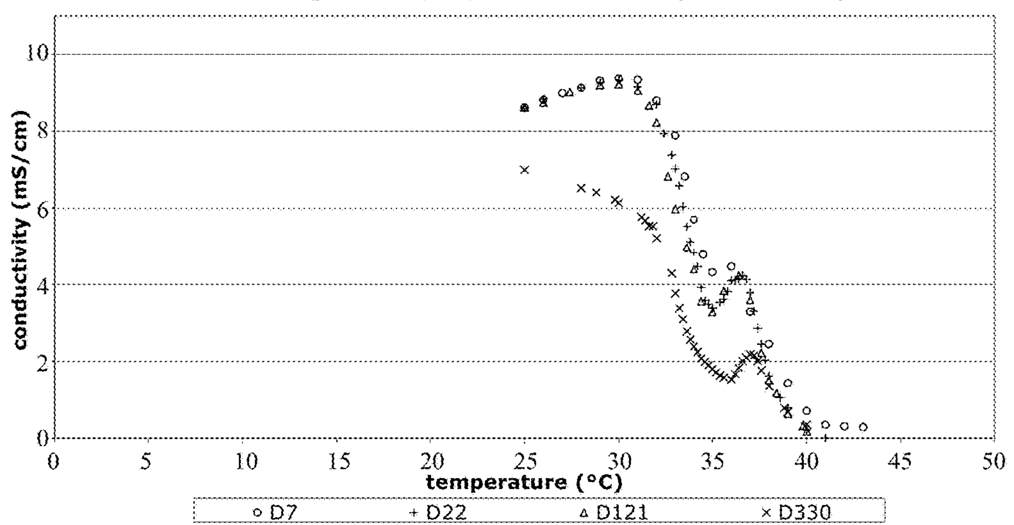
Figure 2:
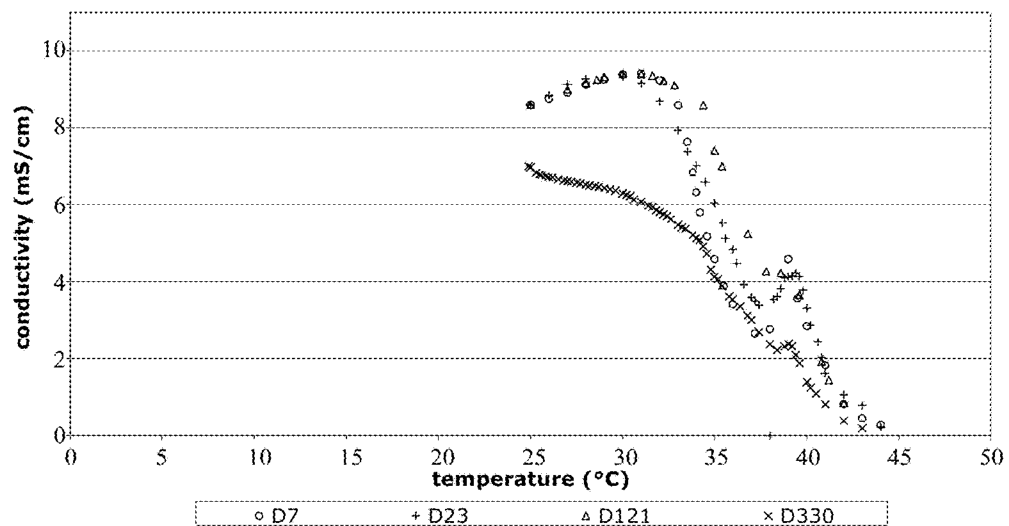
FIG. 2 provides graphs of the PIT determination for the vaccine formulations of trials 3 & 4 on multiple days after production (one year stability study)
Figure 2:
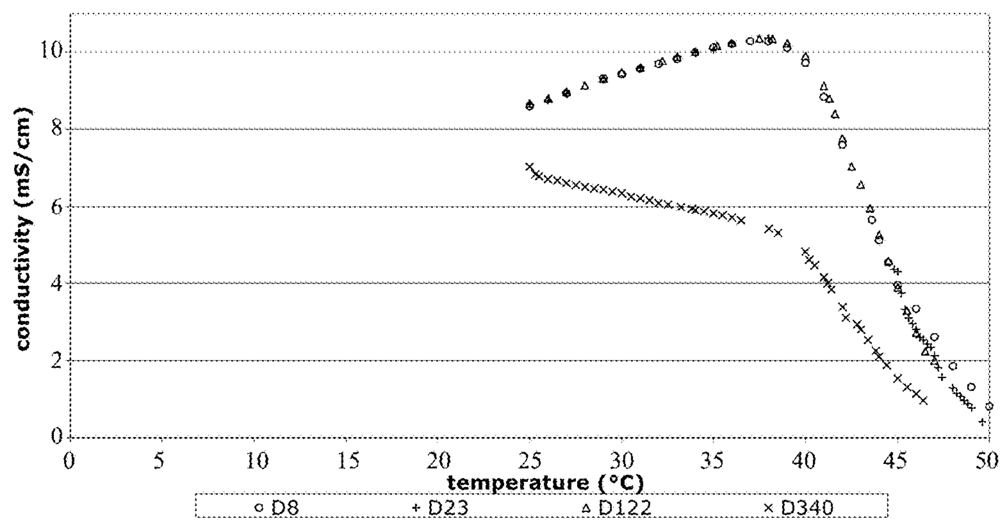
Figure 3:
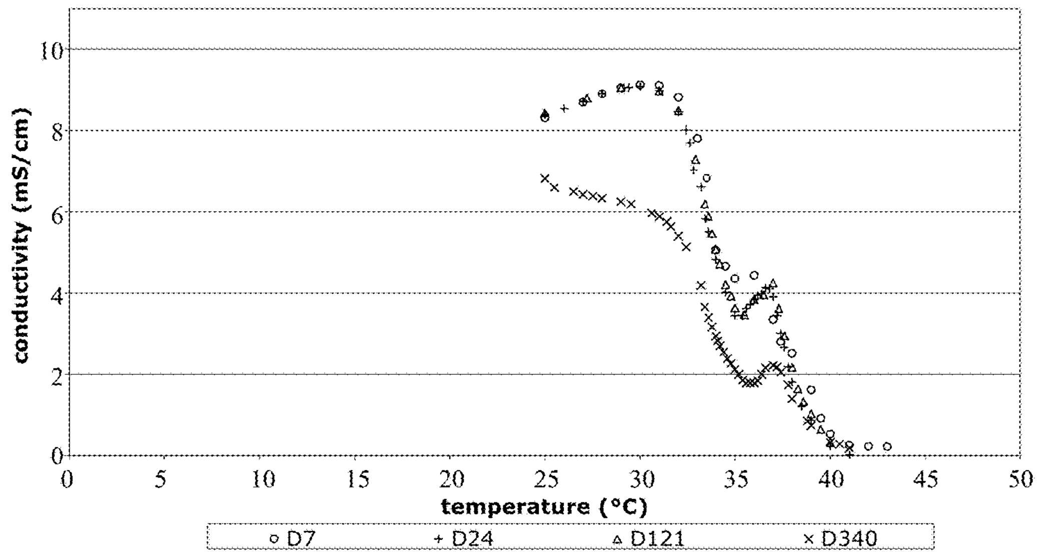
FIG. 3 provides graphs of the PIT determination for the vaccine formulations of trials 5 & 6 on multiple days after production (one year stability study)
Figure 3:
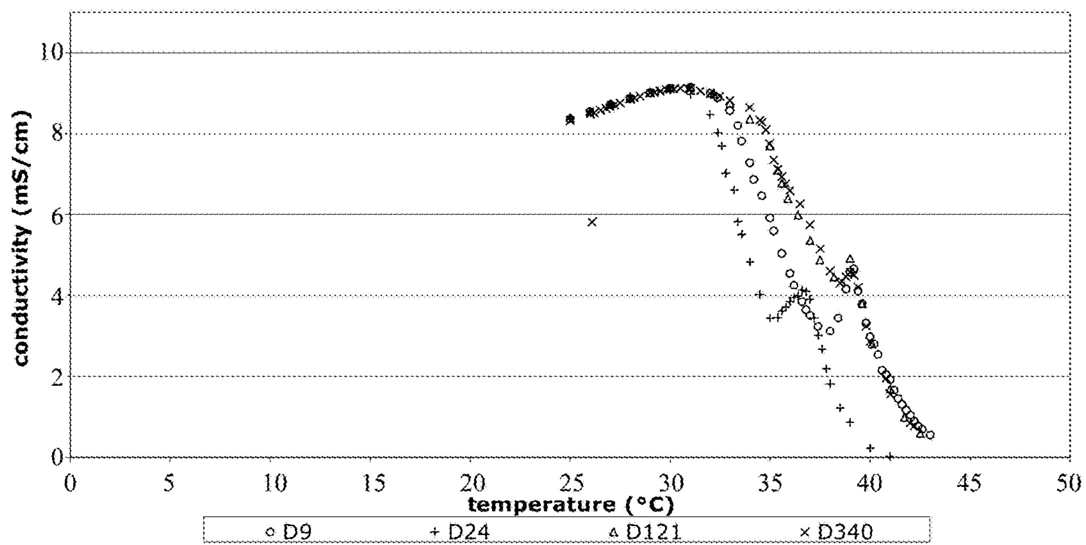
Figure 4:
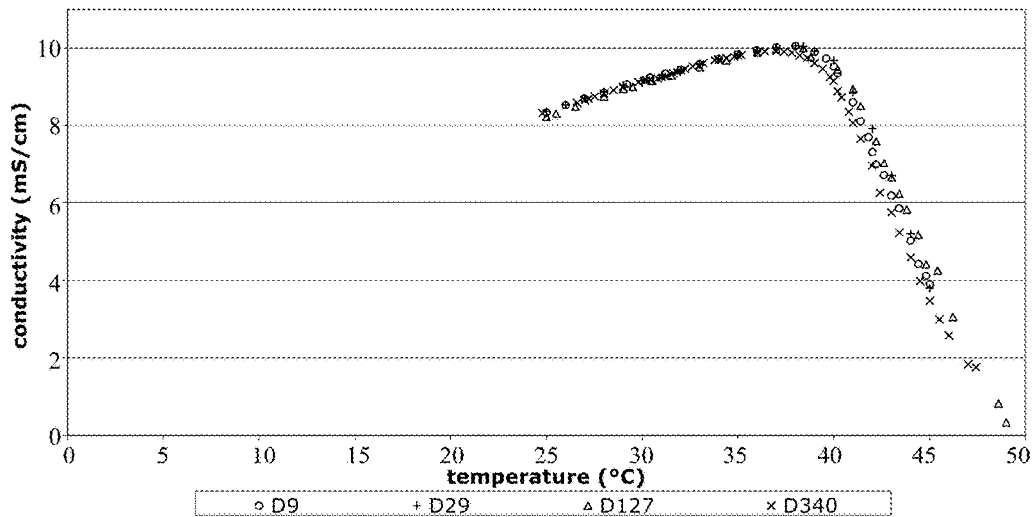
FIG. 4 provides graphs of the PIT determination for the vaccine formulations of trials 7 & 8 on multiple days after production (one year stability study)
Figure 4:
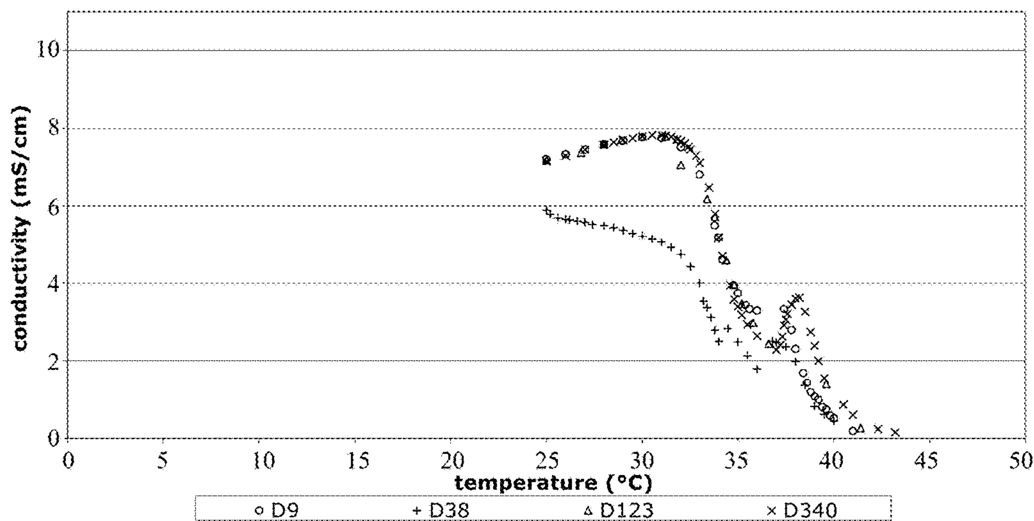
Figure 5:
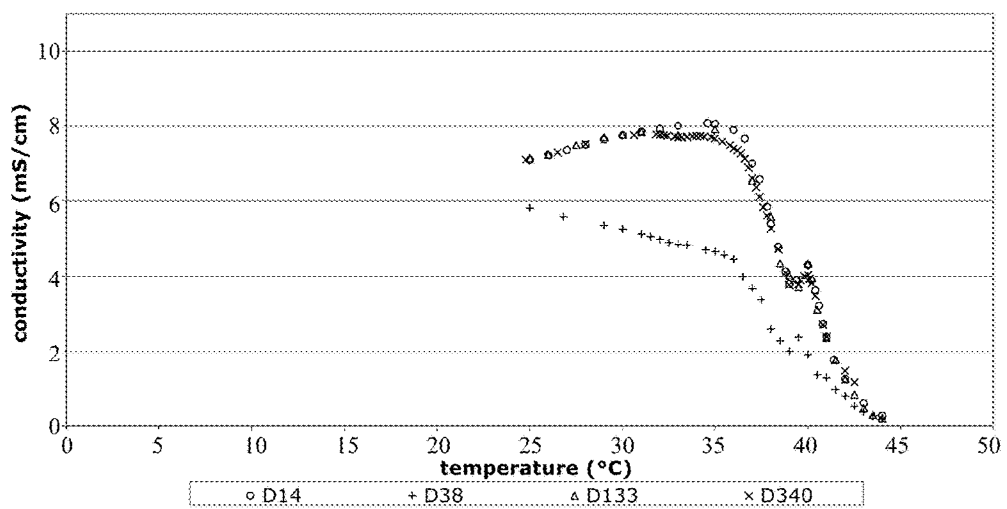
FIG. 5 provides a graph of the PIT determination for the vaccine formulations of trial 9 on multiple days after production (one year stability study)

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents. The contents of all references, published patents, and patents cited throughout the present application are hereby incorporated by reference in their entirety.

For convenience, certain terms employed in the Specification, Examples, and appended Claims are collected here.

As used herein, the term "animal" includes all vertebrate animals including humans. It also includes an individual animal in all stages of development, including embryonic and fetal stages. In particular, the term "vertebrate animal" includes, but not limited to, humans, canines (e.g., dogs), felines (e.g., cats); equines (e.g., horses), bovines (e.g., cow, cattle), porcine (e.g., pigs), as well as in avians. As used herein, the term "cow" or "cattle" is used generally to refer to an animal of bovine origin of any age. Interchangeable terms include "bovine", "calf", "steer", "bull", "heifer", "cow" and the like. Interchangeable terms include "piglet", "sow" and the like. The term "avian" as used herein refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary. The term "pig" or "piglet" means an animal of porcine origin, while "sow" refers to a female of reproductive age and capability.

As used herein, the term "virulent" means an isolate that retains its ability to be infectious in an animal host.

As used herein, the term "inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with formalin), sonication, radiation, heat or any other convention means sufficient to prevent replication or growth of the organism while maintaining its immunogenicity.

As used herein, the term "immunogenicity" means capable of producing an immune response in a host animal against an antigen or antigens. This immune response forms the basis of the protective immunity elicited by a vaccine against a specific infectious organism.

As used herein, the term "immune response" refers to a response elicited in an animal. An immune response may refer to cellular immunity (CMI); humoral immunity or may involve both. The present invention also contemplates a response limited to a part of the immune system. For example, a vaccine composition of the present invention may specifically induce an increased gamma interferon response.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

As used herein, the term "multivalent" means a vaccine containing more than one antigen whether from the same species (i.e., different isolates of FMD virus serotypes), from a different species (i.e., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

As used herein, the term "adjuvant" means a substance added to a vaccine to increase a vaccine's immunogenicity. The mechanism of how an adjuvant operates is not entirely known. Some adjuvants are believed to enhance the immune response by slowly releasing the antigen, while other adjuvants are strongly immunogenic in their own right and are believed to function synergistically. Known vaccine adjuvants include, but are not limited to, oil and water emulsions (for example, complete Freund's adjuvant and incomplete Freund's adjuvant), *Corynebacterium parvum*, Bacillus Calmette Guerin, aluminum hydroxide, glucan, dextran sulfate, iron oxide, sodium alginate, Bacto-Adjuvant, certain synthetic polymers such as poly amino acids and co-polymers of amino acids, saponin, "REGRESSIN" (Vetrepharm, Athens, Ga.), "AVRIDINE" (N,N-dioctadecyl-N',N'-bis(2-hydroxyethyl)-propanediamine), paraffin oil, muramyl dipeptide and the like.

As used herein, the term "emulsion" refers to a combination of at least two substances, wherein a first substance is dispersed in a second substance in which the first substance is insoluble. One example of an emulsion of the present invention is an oil phase dispersed in an aqueous phase.

As used herein, the term "incomplete emulsion" refers to a composition to which at least one additional component must be added to make the "complete emulsion". As used herein, the term "complete emulsion" can be considered equivalent to the "ready-to-use" immunological composition of the present invention. An example of a complete emulsion is an immunological composition according to the present invention that is ready to be administered to an animal according to the methods of the present invention.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

The term "purified" as used herein does not require absolute purity; rather, it is intended as a relative term. Thus, for example, a purified immunogen preparation, such as protein or inactivated virus, is one in which the immunogen is more enriched than the immunogen is in its natural environment. An immunogen preparation is herein broadly referred to as "purified" such that the immunogen represents at least 60%, at least 70%, at least 80%, at least 90%, at least 95%, or at least 98%, of the total immunogen content of the preparation. A "crude preparation", which represents the lowest degree of purification, may contain as little as less than 60%, lest than 20%, less than 10%, less than 5%, or less than 1% of immunogenic components.

The term "highly purified" as used herein is intended to suggest a "higher degree of purity" as compared to the term "moderately purified". This "higher degree of purity" can include, but is in no way limited to, reduced percentages of contaminants, in an immunological preparation that has been "highly purified" versus an immunological preparation that has been "moderately purified". As discussed herein, "highly purified" immunological preparations will have the lowest to undetectable percentages of contaminants that can cause: reduced desired immune response, increased undesired immune response (e.g. hypersensitivity reaction), or reduced formulation stability. Similarly, an immunological preparation that has been "moderately purified" contains relatively reduced percentages of contaminants versus an immunological preparation that has been "minimally purified", which likewise, has reduced percentages of contaminants versus a preparation designated a "crude preparation".

Contaminants in an immunological preparation can include, but are in no way limited to, substances that contribute negatively to an immunological composition according to the present invention. One of several examples of a contaminant contributing negatively would be a contaminant that reduces the ability of an immunological composition of the present invention to elicit an immune response in animals.

Varying levels of purity (e.g. "highly purified", "moderately purified", and the like) can be achieved using various methods. For example, a combination of chromatography and size exclusion gel filtration can result in a "highly purified" or "moderately purified" immunological preparations. Differences in source/type of immunogens, as well as slight variations in purification procedures can significantly affect the final degree of immunogen purity. In general, as used herein, immunological preparations having the lowest to highest percentage of contaminants will be described as 1) "highly purified, 2) "moderately purified", 3) "minimally purified", 4) "crude preparation", respectively. A "highly purified" preparation will have the lowest level across all types of contaminants. A "moderately purified" preparation will have relatively low levels of most types of contaminants, but may have one type of contaminant in higher abundance than would be observed for a comparable "highly purified" preparation. Likewise, a "minimally purified preparation" will have relatively low levels of some types of contaminants, but may have more than one type of contaminant in higher abundance than a comparable "moderately purified" preparation. As expected, a "crude preparation" has the highest level of contaminants, across all contaminant types, as compared to the other types of preparations discussed herein.

The present invention provides a novel oil-in-water (O/W) emulsion comprising:

(1) an aqueous solution comprising a vaccine antigen or immunogen capable of inducing an immune response in a host;
(2) an aqueous solution comprising an ionic surfactant;
(3) a non-ionic hydrophilic surfactant;
(4) a mineral oil;

In one embodiment, the novel oil-in-water (O/W) emulsion comprises:

(1) an aqueous solution comprising a vaccine antigen or immunogen capable of inducing an immune response in a host;
(2) an aqueous solution comprising an ionic surfactant such as saponin;
(3) a non-ionic hydrophilic surfactant having a hydrophilic-lipophilic balance (HLB) value of greater than 13 and less than 40 (HLB>13, in particular HLB≥13.5, and preferably HLB≥14);
(4) a mineral oil;
(5) a non-ionic lipophilic surfactant; and
(6) a non-ionic hydrophilic surfactant having a low HLB value (HLB value between 9 and 13).

In another embodiment the present invention provides a novel oil-in-water (O/W) emulsion comprising:

(1) an aqueous solution comprising a vaccine antigen or immunogen capable of inducing an immune response in a host;
(2) an aqueous solution comprising an ionic surfactant such as saponin
(3) an optional aqueous solution comprising aluminum hydroxide
(4) a non-ionic hydrophilic surfactant having a hydrophilic-lipophilic balance (HLB) value of greater than 13 and less than 40 (HLB>13, in particular HLB≥13.5, and preferably HLB≥14);
(5) a mineral oil;
(6) a non-ionic lipophilic surfactant; and
(7) a non-ionic hydrophilic surfactant having a low HLB value (HLB value between 9 and 13).

Some emulsions made according to the present invention are based on a combination of at least four (4) surfactants chosen among the members of four different groups of surfactants, and it is possible to use one or more surfactant pertaining to each group. Three (3) of these groups comprise non-ionic surfactants and one (1) of these groups comprises ionic surfactants, for example saponins.

In one of several embodiments, the concentration of the ionic surfactant (2) in the emulsion (in the present specification this means the final emulsion comprising all ingredients unless otherwise indicated) is from about 0.01% to about 10%.

In one of several embodiments, the concentration of non-ionic hydrophilic surfactant (7) in the emulsion (in the present specification this means the final emulsion comprising all ingredients unless otherwise indicated) is from 1% to 8%, in particular from 1.5% to 6%, preferably from 2% to 5%, more preferably from 2.5% to 4%, expressed as a percentage in weight by volume of emulsion (w/v).

This group of surfactants comprises non-ionic hydrophilic surfactants having a low HLB value (HLB value between 9 and 13). This group includes but is not limited to ethoxylated fatty acid monoester of sorbitan (in particular 5 ethoxyl groups) (e.g. ethoxylated sorbitan monooleate such as TWEEN 81®, ethoxylated fatty acid diesters of sorbitan, ethoxylated fatty acid triesters of sorbitan (in particular 20 ethoxyl groups) (e.g. ethoxylated sorbitan trioleate such as TWEEN 85®), ethoxylated sorbitan tristearate such as TWEEN 65®, ethoxylated fatty alcohols (in particular 5-10 ethoxyl groups) (e.g. BRIJ 76®, BRIJ 56®, BRIJ 96®), ethoxylated fatty acids (in particular 5-10 ethoxyl groups) (e.g. Simulsol 2599®, MYRJ 45®), ethoxylated castor oil (in particular 25-35 ethoxyl groups) (e.g. ARLATONE 650®, ARLATONE G®), and combinations thereof.

Ethoxylated fatty acid diesters of sorbitan and ethoxylated fatty acid triesters of sorbitan are preferred, as well combinations of both species. The fatty acid is preferably selected from the group consisting of oleate, palmitate, stearate, isostearate, laurate and the combinations thereof. Preferred ethoxylated fatty acid triester of sorbitan comprise ethoxylated sorbitan trioleate such as TWEEN 85®), or ethoxylated sorbitan tristearate such as TWEEN 65®.

In one of several embodiments, the concentration of non-ionic hydrophilic surfactant (4) is generally from 0.1% to 1.5%, in particular from 0.2% to 1.4%, preferably from 0.3% to 1.3%, more preferably from 0.4% to 1.2%, expressed as a percentage in weight by volume of emulsion (w/v).

This second group of surfactants comprises non-ionic hydrophilic surfactants having a high hydrophilic-lipophilic balance (HLB) value (HLB>13, in particular HLB≥13.5, and preferably HLB≥14). This group comprises ethoxylated fatty acid monoesters of sorbitan (in particular 20 ethoxyl groups) (e.g. ethoxylated sorbitan monolaurate such as TWEEN 20®, ethoxylated sorbitan monopalmitate such as TWEEN 40®, ethoxylated sorbitan monostearate (such as TWEEN 60®, ethoxylated sorbitan monooleate such as TWEEN 80®, ethoxylated fatty alcohols (in particular 15-30 ethoxyl groups) (e.g. BRIJ 78®, BRIJ 98®, BRIJ 721®), ethoxylated fatty acids (in particular 15-30 ethoxyl groups) (e.g. MYRJ 49®, MYRJ 51®, MYRJ 52®, MYRJ 53®), non-ionic block-copolymers (e.g. polyoxyethylene/polyoxypropylene copolymer (POE-POP), such as LUTROL F127®, LUTROL F68®), and combinations thereof.

For the non-ionic block-copolymers, the percentages may be lower and be in particular from 0.1% to 0.5%, more particularly from 0.2% to 0.4% (weight by volume of emulsion (w/v)).

Preferred surfactants (4) comprise ethoxylated fatty acid monoesters of sorbitan, such as those described above.

In one of several embodiments, the concentration of non-ionic lipophilic surfactant (6) is from 0.1% to 2.5%, in particular from 0.2% to 2%, preferably from 0.2% to 1.5%, more preferably from 0.2% to 1.2%, expressed as a percentage in weight by volume of emulsion (w/v).

This group of surfactants comprises fatty acid esters of sorbitan (e.g. sorbitan monolaurate, like SPAN 20®, sorbitan monopalmitate, such as SPAN 40®, sorbitan monostearate, such as SPAN 60®, sorbitan tristearate, such as SPAN 65®, sorbitan monooleate, like SPAN 80®, sorbitan trioleate, like SPAN 85®, sorbitan monoisostearate, such as ARLACEL 987®, sorbitan isostearate, such as CRILL 6®), fatty acid esters of mannide (e.g. MONTANIDE 80®, mannide monooleate (such as ARLACEL A®), mannide dioleate, mannide trioleate, mannide tetraoleate), ethoxylated fatty acid esters of mannide (2, 3 or 4 ethoxyl groups) (e.g. MONTANIDE 888®, MONTANIDE 103®, ethoxylated mannide monooleate, ethoxylated mannide dioleate, ethoxylated mannide trioleate, ethoxylated mannide tetraoleate), and combinations thereof.

The fatty acid is preferably selected from the group consisting of oleate, palmitate, stearate, isostearate, laurate and combinations thereof.

Preferred surfactants (6) comprise the fatty acid esters of sorbitan, in particular those described above, and combinations thereof.

The surfactants of the invention may have fatty acids from animal or vegetal origin. The change of one origin for the other (for example animal TWEEN 80® to vegetal TWEEN 80®) could be done simply with only minor adjustment in the formulation of the emulsion.

An emulsion according to the invention may have an overall concentration of surfactants, by weight per volume of emulsion, from 1.2% to 10%, in particular from 2% to 8%, preferably from 3% to 7%, more preferably from 4% to 6%.

Generally, the emulsion according to the invention may have a phase inversion temperature (PIT) which is ≥33° C., in particular ranges from 33° C. to 65° C., more particularly from 36° C. to 60° C., preferably from 37° C. to 55° C., and more preferably from 38° C. to 50° C.

The PIT is the temperature at which a water-in-oil emulsion changes to an oil-in-water emulsion or de-phases (breaks of the emulsion and separation of the 2 phases). The PIT value may be measured by various means, like for example by visual appearance (e.g. see example 2) or by conductivity. The emulsion is placed at a temperature below the PIT of the emulsion, for example of about 25° C. in a water-bath. The temperature is progressively increased. The change of the visual aspect of the emulsion is observed in comparison with a control emulsion, notably the fluidity, the viscosity, the separation in two phases, the change of the surface aspect due to the migration of the oily phase to the surface. The temperature, for which this change of visual aspect was observed, is the PIT value of the emulsion. Alternatively, the PIT is determined by the quick passage from a conductivity value of about 5-8 milliSiemens/centimeter (mS/cm) (oil-in-water emulsion) to a value of about 0 mS/cm (water-in-oil emulsion) measured by a probe placed into the emulsion, near its surface. The temperature, for which the transition was observed, is the PIT value of the emulsion. One of ordinary skill n the art will be able to determine combinations of surfactants and oil, including their respective concentrations, in order to produce emulsions according to the invention, and in particular emulsions having a PIT value within the ranges defined above without undue experimentation.

Generally, emulsions according to the present invention may contain, by volume per volume of emulsion, from 3% to 55% of oil, in particular from 5% to 50% of oil, preferably from 10% to 40% of oil and, more preferably, from 20% to 40% of oil. By definition, ranges of values in the present specification include always the limit of the range, unless otherwise indicated.

The oil used may be a mineral oil including, but not limited to, paraffin oil such as isoparaffinic oil and/or naphtenic oil, squalane, pristane, polyisobutene oil, hydrogenated polyisobutene oil, polydecene oil, polyisoprene oil, polyisopropene oil and the like. One advantageous mineral oil useful in the present invention may include an oil comprising a linear or ramified carbon chain having a number of carbon atoms greater than 15, preferably from 15 to 32, and free of aromatic compounds. Such oils may, for example, be those marketed under the name "MARCOL 52®" or "MARCOL 82®" (produced by Esso, France) or "DRAKEOL 6VR®" or "DRAKEOL 5®" "DRAKEOL 7®" (produced by Penreco, USA), "CLEAROL®" (produced by Sonneborn, USA), "Paraffin Oil Codex AAB2®" (produced by Aiglon, France), BLANDOL (produced by Sonneborn, USA), ONDINA 915 (produced by Shell, UK).

The oil may also be a mixture of oils comprising at least 2 oils selected among the oils described herein, and in any proportion. The mixture of oils may also comprise at least one oil selected among the oils described above and at least one vegetable oil, and this vegetable oil represents from about 0.1% to about 33% of the oily phase, preferably from about 10% to about 25% v/v. These vegetable oils are unsaturated oils rich in oleic acid that are biodegradable and preferably liquid at the storage temperature (about +4° C.) or at least make it possible to give emulsions that are liquid at this temperature. For example the vegetable oil may be groundnut oil, nut oil, sunflower oil, safflower oil, soya oil, onager oil and the like.

In one of several embodiments, hydrophilic surfactants (4) and (7) preferably include surfactants having the same hydrophilic part of the molecules. For instance, use is made of ethoxylated fatty acid esters of sorbitan for each of hydrophilic surfactants (4) and (7). For example if TWEEN 85® is chosen as non-ionic hydrophilic surfactants having a low HLB value, the non-ionic hydrophilic surfactant having a high HLB value will advantageously have a hydrophilic part constituted with an ethoxylated sorbitan, such as TWEEN 80®.

Generally, the present invention envisions using an aqueous solution comprising a suitable veterinary or pharmaceutically acceptable vehicle, excipient, or diluent including, but not limited to, sterile water, physiological saline, glucose, buffer and the like. The vehicle, excipient or diluent may also include polyols, glucids or pH buffering agents. The vehicle, excipient or diluent may, for example, also comprise amino acids, peptides, antioxidants, bactericide, and bacteriostatic compounds. The aqueous solution is added to the oil and the surfactants in quantity to obtain 100% of the volume of the emulsion according to the invention.

The hydrophilic-lipophilic balance (HLB) of an emulsion allows for the estimation of the hydrophilic or lipophilic force of a surfactant. The HLB of an amphiphilic molecule is generally calculated as follow:

$$HLB = \frac{(20 \times \text{weight of the hydrophilic part})}{(\text{weight of the amphiphilic molecule})}$$

The HLB may have a value ranging from 0 (for the most lipophilic molecule) to 20 (for the most hydrophilic molecule). According to the chemical composition of the surfactant (notably for example the addition of ethoxyl groups or of alkene oxides), this estimation may change and the domain of HLB value may increase (for example, the LUTROL F68® has a HLB of 29). With a mixture of surfactants, the HLB of the mixture is the addition of the HLB of each surfactant, balanced by its weight ratio:

$$HLB = \frac{(HLB \text{ surfactant } X \times \text{weight surfactant } X) + (HLB \text{ surfactant } Y \times \text{weight surfactant } Y)}{(\text{weight surfactant } X + \text{weight surfactant } Y)}$$

In one embodiment of an emulsion made according to the present invention, the final HLB of the emulsion is from about 9 to about 12, preferably from about 9.5 to about 11.5 and more preferably from about 10 to about 11.5.

The present invention contemplates an emulsion comprising a paraffin oil (in particular at a concentration of from about 10% to about 40% and preferably from about 20% to about 40%, expressed as a volume per volume of emulsion (v/v)); a sorbitan fatty acid monoester (as non-ionic lipophilic surfactant), an ethoxylated fatty acid triester of sorbitan (as non-ionic hydrophilic surfactant having a low HLB value); and an ethoxylated fatty acid monoester of sorbitan (as non-ionic hydrophilic surfactant having a high HLB value). In particular the sorbitan fatty acid monoester is a sorbitan monooleate (in particular at the concentration from 0.2% to 1.5%, preferably from 0.2% to 1.2% expressed as a weight per volume of emulsion (w/v)), the ethoxylated fatty acid triester of sorbitan is an ethoxylated trioleate of sorbitan (in particular at the concentration from 2% to 5%, preferably from 2.5% to 4% w/v)) and the ethoxylated fatty acid monoester of sorbitan is an ethoxylated sorbitan monooleate (in particular at the concentration from 0.3% to 1.3%, preferably from 0.4% to 1.2% w/v). For example the emulsion comprises the paraffin oil at about 29.3% by volume per volume of emulsion, the sorbitan monooleate at 0.6% by weight per volume of emulsion, the ethoxylated trioleate of sorbitan at 3.4% by weight per volume of emulsion, and the ethoxylated sorbitan monooleate at 0.75% by weight per volume of emulsion.

In a second embodiment according to the present invention, the emulsion comprises a paraffin oil (in particular at a concentration from 10% to 40%, preferably from 20% to 40% v/v), a sorbitan fatty acid monoester (as non-ionic lipophilic surfactant), an ethoxylated fatty acid triester of sorbitan (as non-ionic hydrophilic surfactant having a low HLB value), and a non-ionic block-copolymer (as non-ionic hydrophilic surfactant having a high HLB value). In particular the sorbitan fatty acid monoester is a sorbitan monooleate (in particular at the concentration from 0.2% to 1.5%, preferably from 0.2% to 1.2% w/v), the ethoxylated fatty acid triester of sorbitan is an ethoxylated trioleate of sorbitan (in particular at the concentration from 2% to 5%, preferably from 2.5% to 4% w/v) and the non-ionic block-copolymer is a polyoxyethylene/polyoxypropylene polymer (POE-POP) (in particular at the concentration from 0.1% to 0.5%, preferably from 0.2% to 0.4% w/v). For example the emulsion comprises the paraffin oil at about 29.3% v/v, the sorbitan monooleate at 0.6% w/v, the ethoxylated trioleate of sorbitan at 3.4% w/v, and the ethoxylated sorbitan monooleate at 0.25% w/v.

In a particular embodiment, the invention contemplates an injectable oil-in-water (O/W) emulsion comprising:

(1) an aqueous solution comprising an active ingredient such as a drug or an immunogen, preferably an immunogen;
(2) an aqueous solution comprising saponin
(3) a mineral oil;
(4) a non-ionic lipophilic surfactant; and
(5) a non-ionic hydrophilic surfactant having a low HLB value which comprises of an ethoxylated fatty acid diester of sorbitan (which may have a HLB value between 11 and 13).

In another particular embodiment, the invention contemplates an injectable oil-in-water (O/W) emulsion comprising:

(1) an aqueous solution comprising an active ingredient such as a drug or an immunogen, preferably an immunogen;
(2) an aqueous solution comprising saponin
(3) an aqueous solution comprising aluminum hydroxide
(4) a mineral oil;
(5) a non-ionic lipophilic surfactant; and
(6) a non-ionic hydrophilic surfactant having a low HLB value which comprises of an ethoxylated fatty acid diester of sorbitan (which may have a HLB value between 11 and 13).

An emulsion according to this embodiment comprises ethoxylated fatty acid diesters of sorbitan that may contain up to 20 ethoxy groups. The fatty acids may be from animal or vegetable origin and may be selected from the group consisting of oleate, palmitate, stearate, isostearate, laurate and combinations thereof. In one embodiment the ethoxylated fatty acid is preferably oleate. The other ingredients, as well as the general properties of the emulsion such as the PIT, may have the same characteristics than those described above.

Preferably, surfactant (6) comprises ethoxylated fatty acid diesters of sorbitan, such as ethoxylated sorbitan dioleate, ethoxylated sorbitan distearate or ethoxylated sorbitan diisostearate, ethoxylated sorbitan dipalmitate, ethoxylated sorbitan dilaurate, and combinations thereof.

Optionally other compounds may be added as co-adjuvants to the emulsion, including, but not limited to, alum; CpG oligonucleotides (ODN), in particular ODN 2006, 2007, 2059, or 2135 (Pontarollo R. A. et al., *Vet. Immunol. Immunopath,* 2002, 84: 43-59; Wernette C. M. et al., *Vet. Immunol. Immunopath,* 2002, 84: 223-236; Mutwiri G. et al., *Vet. Immunol. Immunopath,* 2003, 91: 89-103); polyA-polyU ("Vaccine Design The Subunit and Adjuvant Approach", edited by Michael F. Powell and Mark J. Newman, *Pharmaceutical Biotechnology,* 6: 03); dimethyldioctadecylammonium bromide (DDA) ("Vaccine Design: The Subunit and Adjuvant Approach", edited by Michael F. Powell and Mark J. Newman, *Pharmaceutical Biotechnology*, volume 6: 157), N,N-dioctadecyl-N',N'-bis(2-hydroxyethyl) propanediamine (such as AVRIDINE®) (Ibid, p. 148), carbomer, chitosan (see U.S. Pat. No. 5,980,912 for example).

The present invention also provides a method of making a vaccine composition or immunologic composition comprising at least one antigen or immunogen composition and an adjuvant or emulsion made according to the present invention. The antigen or immunogen composition may be incorporated during emulsion formation or, in an alternate embodiment, the antigen or immunogen composition, preferably additionally comprising saponin and optionally additionally comprising aluminum hydroxide, may be added to the emulsion later as, for example, just before use.

The entire amount of the aqueous solution used may be present in the emulsion first produced. Or it may be that only a part of this aqueous solution is used to form the emulsion, and the remaining quantity of aqueous solution is added after incorporation of the immunogen. The immunogen or antigen may be in a dry form or present in some other appropriate solid form and then mixed with the emulsion or, alternately, the antigen may be in solution, in particular in an aqueous solution, and this solution mixed with the emulsion.

Surfactants are preferably added to either the oil or the aqueous solution according to their solubility. For example, the non-ionic lipophilic surfactants are added to the oil according to the invention while non-ionic hydrophilic surfactants having a high HLB value are added to the aqueous solution.

The emulsification can be prepared according to conventional methods known to one of ordinary skill in the art. For example, in one embodiment of the present invention, the emulsion can be prepared at a temperature below the PIT of the emulsion, in particular at room temperature, e.g. at about 25° C. The aqueous phase and the oily phase are mixed together by a mechanical agitation, e.g. with a turbine equipped with a rotor-stator able to create a high shearing force. Preferably the agitation starts at a low rotation speed and slowly increases in relation to the progressive addition generally of the aqueous solution in the oil. Preferably the aqueous solution is progressively added to the oil. The ratio of oil/aqueous solution may be adapted to obtain a water-in oil (W/O) emulsion, for example, at a concentration of about 40% to about 55% of oil (v/v). When the agitation is stopped, the emulsion changes progressively to an O/W emulsion (phase inversion). After inversion and if needed, the emulsion is diluted by addition of an aqueous solution to obtain the desired concentration of oil into the final emulsion. The emulsion may be stored at about 5° C.

In another embodiment, the emulsion can be prepared at a temperature higher than the PIT of the emulsion. In a first step, the aqueous phase and the oily phase are mixed together at a temperature higher than the PIT of the emulsion. Preferably the aqueous solution is progressively added to the oil. The ratio of oil/aqueous solution may be adapted to obtain a water-in oil (W/O) emulsion, for example at a concentration of about 40% to about 55% of oil (v/v). The emulsification may be done by an agitation with low or no shearing force, e.g. with a static mixer or a marine helix or with a turbine at a very low rotation speed. The emulsion obtained is a water-in-oil (W/O) emulsion. In a second step, the emulsion is cooled progressively below the PIT. During this step, the emulsion changes to an O/W emulsion (phase inversion). After inversion and if needed, the emulsion is diluted by addition of an aqueous solution to obtain the desired concentration of oil into the final emulsion. The emulsion may be stored at about 5° C.

The size of the droplets in the emulsion may be from about 100 nm to about 500 nm. The emulsion may be used, for example, as an adjuvant to formulate a vaccine composition or a pharmaceutical composition. The emulsion may also be used as a solvent to dissolve a dried product, especially a dry product containing, for example, attenuated microorganisms or live recombinant vectors.

In a particular embodiment, a pre-emulsion is produced with only a part of the aqueous solution. This pre-emulsion may be diluted by addition of a suspension of an active ingredient such as a drug or an immunogen, preferably an immunogen, to obtain the final composition. Alternatively, the pre-emulsion may be diluted with an aqueous solution and used to dissolve a dried product such as a dry product.

The immunogen or antigen suitable for use in the present invention may be selected from the group consisting of inactivated pathogens, attenuated pathogens, immunogenic sub-units (e.g. proteins, polypeptides, peptides, epitopes, haptens), or recombinant expression vectors, including plasmids having immunogenic inserts. In one embodiment of the present invention, the immunogen is an inactivated or killed microorganism. In another embodiment of the invention, the vaccine composition comprises an immunogen selected from the group of avian pathogens including, but not limited to, *Salmonella typhimurium, Salmonella enteritidis*, Infectious Bronchitis virus (IBV), Newcastle Disease virus (NDV), egg drop syndrome virus (EDS), or Infectious Bursal Disease virus (IBDV), avian influenza virus, and the like, and combinations thereof.

Alternately, the vaccine composition comprises an immunogen selected from a feline pathogen such as, but not limited to, feline herpesvirus (FHV), feline calicivirus (FCV), feline leukemia virus (FeLV), feline immunodeficiency virus (FIV), rabies virus, and the like, and combinations thereof.

In yet another embodiment, a vaccine composition of the present invention comprises an immunogen selected from a canine pathogen including, but not limited to, rabies virus, canine herpesvirus (CHV), canine parvovirus (CPV), canine coronavirus, *Leptospira canicola, Leptospira icterohaemorragiae, Leptospira grippotyphosa, Borrelia burgdorferi, Bordetella bronchiseptica* and the like, and combinations thereof.

In yet another embodiment of the invention the composition comprises an immunogen selected from an equine pathogen, such as equine herpesvirus (type 1 or type 4), equine influenza virus, tetanus, west nile virus, and the like or combinations thereof.

In yet another embodiment of the invention, the composition comprises an immunogen selected from an bovine pathogen, such as foot and mouth disease virus (FMDV), rabies virus, bovine rotavirus, bovine parainfluenza virus type 3 (bPIV-3), bovine coronavirus, bovine viral diarrhea virus (BVDV), bovine respiratory syncytial virus (BRSV), Infectious Bovine Rhinotracheitis virus (IBR), *Escherichia coli, Pasteurella multocida, Pasteurella haemolytica* and the like and combinations thereof.

In still another embodiment of the present invention, the composition comprises an immunogen selected from an porcine pathogen such as, but not limited to, swine influenza virus (SIV), porcine circovirus type 2 (PCV-2), porcine reproductive respiratory syndrome virus (PRRS), pseudorabies virus (PRV), porcine parvovirus (PPV), FMDV, *Mycoplasma hyopneumoniae, Erysipelothrix rhusiopathiae, Pasteurella multocida, Bordetella bronchiseptica, Escherichia coli* and the like, and combinations thereof.

Another embodiment of the invention provides for vaccine compositions comprising at least one immunogen and an emulsion in a pharmaceutically acceptable vehicle. Immunogens comprising viruses, bacteria, fungi and the like may be produced by in vitro culture methods using appropriate culture medium or host cells lines and conventional methods well known to those of ordinary skill in the art. For example, PRRS may be cultured in an appropriate cell line, such as MA-104 cell line (see U.S. Pat. Nos. 5,587,164; 5,866,401; 5,840,563; 6,251,404 among others). In a similar manner, PCV-2 may be cultured using PK-15 cells line (see U.S. Pat. No. 6,391,314); SIV may be cultured on eggs (U.S. Pat. No. 6,048,537); and *Mycoplasma hyopneumoniae* may be cultured in a appropriate culture medium (U.S. Pat. No. 5,968,525; U.S. Pat. No. 5,338,543; Ross R. F. et al., *Am. J. Vet. Res.,* 1984, 45: 1899-1905).

In order to obtain an inactivated immunologic, or vaccine composition, the pathogen is preferably inactivated after harvesting and, optionally, subjected to clarification by means of a chemical treatment using, for example, formalin or formaldehyde, beta-propiolactone, ethyleneimine, binary ethyleneimine (BEI), and/or a physical treatment (e.g. a heat treatment or sonication). Methods for inactivation are well known to those of skill in the art. For example, the FMD virus may be inactivated by ethyleneimine (Cunliffe, H R, *Applied Microbiology,* 1973, p. 747-750) or by high pressure (Ishimaru et al., *Vaccine* 22 (2004) 2334-2339), the PRRS virus may be inactivated by beta-propiolactone treatment (Plana-Duran et al., *Vet. Microbiol.,* 1997, 55: 361-370) or by BEI treatment (U.S. Pat. No. 5,587,164); inactivation of PCV-2 virus may be accomplished using ethyleneimine treatment or by beta-propiolactone treatment (U.S. Pat. No. 6,391,314); swine influenza virus may be inactivated using a detergent like Triton, or with formaldehyde treatment (U.S. Pat. No. 6,048,537); *Mycoplasma hyopneumoniae* bacterium may be inactivated by formaldehyde treatment (Ross R. F. supra), by ethylenimine or BEI treatment (see WO 91/18627).

The inactivated pathogen can be concentrated by conventional concentration techniques, in particular by ultrafiltration, and/or purified by conventional purification means, in particular using chromatography techniques including, but not limited to, gel-filtration, ultracentrifugation on a sucrose gradient, or selective precipitations, in particular in the presence of polyethylene glycol (PEG).

Immunogens useful in vaccine compositions according to the present invention also include expression vectors. Such vectors include, but are not limited to, in vivo recombinant expression vectors such as a polynucleotide vector or a plasmid (EP-A2-1001025; Chaudhuri P, *Res. Vet. Sci.* 2001, 70: 255-6), virus vectors such as, but not limited to, adenovirus vectors, poxvirus vectors such as fowlpox (U.S. Pat. Nos. 5,174,993; 5,505,941; and 5,766,599) or canarypox vectors (U.S. Pat. No. 5,756,103) or bacterial vectors (*Escherichia coli* or *Salmonella* sp.)

The present invention also encompasses the formulation of multivalent immunological compositions or combination vaccine compositions. For example, antigens useful in a combination bovine bacterin made according to the present invention include, but are not limited to, *Mycoplasma bovis, Pasteurella* sp., particularly *P. multocida* and *P. haemolytica, Haemophilus* sp., particularly *H. somnus, Clostridium* sp., *Salmonella, Corynebacterium, Streptococcus, Staphylococcus, Moraxella, E. coli* and the like.

The present invention further provides for methods for inducing an immune response in a host, e.g., an animal, comprising administering to the host an immunological composition or a vaccine composition according to the invention. The immune responses elicited in this manner are notably antibody and/or cellular immune responses, and in particular, a gamma-interferon response.

In particular, the present invention provides for methods to immunize against, or to prevent or to reduce the symptoms caused by, infection of an animal with a pathogenic organism (for example, infection by a virus, bacteria, fungus, or protozoan parasite). The method of the present invention is useful in vertebrate animals including, but not limited to, humans, canines (e.g., dogs), felines (e.g., cats); equines (e.g., horses), bovines (e.g., cattle) and porcine animals (e.g., pigs), as well as in avians including, but not limited to, chickens, turkeys, ducks, geese, a quail, a pheasant, parrots, finches, hawks, crows and ratites (ostrich, emu, cassowary, and the like).

In a particular aspect of the invention, these methods consist of the vaccination of pregnant females before parturition by administering a vaccine composition made according to the invention. These methods further include the induction of protective antibodies elicited by the vaccination protocol and the transfer of these protective antibodies from vaccinated pregnant females to their offspring. The transfer of such maternal antibodies subsequently protects the offspring from disease.

The dosage of the vaccine composition made according to the present invention will depend on the species, breed, age, size, vaccination history, and health status of the animal to be vaccinated. Other factors like antigen concentration, additional vaccine components, and route of administration (i.e., subcutaneous, intradermal, oral, intramuscular or intravenous administration) will also impact the effective dosage. The dosage of vaccine to administer is easily determinable based on the antigen concentration of the vaccine, the route of administration, and the age and condition of the animal to be vaccinated. Each batch of antigen may be individually calibrated. Alternatively, methodical immunogenicity trials of different dosages, as well as $LD_{50}$ studies and other screening procedures can be used to determine effective dosage for a vaccine composition in accordance with the present invention without undue experimentation. From the examples presented below, it will be readily apparent what approximate dosage and what approximate volume would be appropriate for using the vaccine composition described herein. The critical factor is that the dosage provides at least a partial protective effect against natural infection, as evidenced by a reduction in the mortality and morbidity associated with natural infection. The appropriate volume is likewise easily ascertained by one of ordinary skill in the art. For example, in avian species the volume of a dose may be from about 0.1 ml to about 0.5 ml and, advantageously, from about 0.3 ml to about 0.5 ml. For feline, canine and equine species, the volume of a dose may be from about 0.2 ml to about 3.0 ml, advantageously from about 0.3 ml to about 2.0 ml, and more advantageously, from about 0.5 ml to about 1.0 ml. For bovine and porcine species, the volume of dose may be from about 0.2 ml to about 5.0 ml, advantageously from about 0.3 ml to about 3.0 ml, and more advantageously from 0.5 ml to about 2.0 ml.

Repeated vaccinations may be preferable at periodic time intervals to enhance the immune response initially or when a long period of time has elapsed since the last dose. In one embodiment of the present invention, the vaccine composition is administered as a parenteral injection (i.e., subcutaneously, intradermally, or intramuscularly). The composition may be administered as one dose or, in alternate embodiments, administered in repeated doses of from about two to about five doses given at intervals of about two to about six weeks, preferably from about two to about five weeks. However, one of skill in the art will recognize that the number of doses and the time interval between vaccinations depends on a number of factors including, but not limited to, the age of the animal vaccinated; the condition of the animal; the route of immunization; amount of antigen available per dose; and the like. For initial vaccination, the period will generally be longer than a week and preferably will be between about two to about five weeks. For previously vaccinated animals, a booster vaccination, before or during pregnancy, at about an annual interval may be performed.

The present invention also contemplates administering a vaccine composition using a needlefree injector such as PIGJET®, AVIJET®, DERMOJET® or BIOJECTOR® (Bioject, Oregon, USA). An person of ordinary skill in the art is able to adjust the specifications of the injector as required with regard to factors such as the species of the animal to be vaccinated; the age and weight of the animal, and the like without undue experimentation.

In one embodiment of the present invention, the method comprises a single administration of a vaccine composition formulated with an emulsion according to the invention. For example, in one embodiment, the vaccine composition is an inactivated FMD virus composition, while an alternate embodiment provides for a vaccine comprising an inactivated PCV2 virus composition. Other immunological compositions or vaccines are suitable for use in a single dose regimen including, but not limited to, inactivated *Mycoplasma hyopneumoniae*, PRRS and SIV.

The invention further relates to methods to treat a host, e.g., an animal, comprising administering to the host a pharmaceutical composition made according to the invention and comprising at least one immunogen selected from the group consisting of proteins or peptides, inactivated or attenuated virus, antibodies, allergens, CpG ODN, growth factors, cytokines, or antibiotics, and in particular CpG ODN or cytokines. These pharmaceutical compositions can be used to improve growth performances in an animal such as a chicken, a pig, a cow or cattle.

The present invention further relates to a kit comprising a single vial containing an ingredient such as a purified immunogen combined with an emulsion made according to the present invention. The kit can alternatively comprise a first vial containing an ingredient such as an immunogen or pharmaceutical composition, combined with saponin and aluminum hydroxide, and a second vial containing an emulsion made according to the present invention. The immunogen may be in a dry form, a dried form or in aqueous solution as described herein.

The invention will now be further described by way of the following non-limiting examples.

Example 1

Emulsion Manufacturing Method

The emulsion was prepared by Inversion method. In a first step, the aqueous phase and the oily phase were mixed together at +40° C. In a second step, the emulsion was cooled progressively below the PIT at +5° C. in order to obtain an O/W emulsion. After inversion, the final emulsion (i.e. vaccine formulation) was mixed and subsequently stored at +5° C. (summarized in Table 1).

TABLE 1

| | Percent for Each Phase | Percent Total (v/v) |
|---|---|---|
| Incomplete Emulsion - Oily phase (120 mL): | | 33 |
| Sorbitan monooleate (SPAN 80 ®) | 1.8% w/v | |
| Sorbitan trioleate (20 OE) (TWEEN 85 ®) | 10.2% w/v | |
| Paraffin oil (MARCOL 82 ®) | 88% v/v | |
| Incomplete Emulsion - Aqueous phase #1 (120 mL): | | 33 |
| 20% (w/v) solution of sorbitan monooleate (20 OE) (TWEEN 80 ®) | 11.25% w/v | |
| Phosphate disodic and monopotassic 0.02M isotonic buffer (pH 7.8) | 85.75% v/v | |
| Incomplete Emulsion = Oily + Aqueous #1 | | 66 |
| Ratio Incomplete Emulsion/Final Emulsion (i.e. Vaccine Formulation) | 2/3 | |
| Add Aqueous phase #2 (120 mL): [Phosphate disodic and monopotassic 0.02M isotonic buffer pH 7.8, saponin, aluminum hydroxide, antigens, M102]* | | 33 |
| Incomplete Emulsion (Oily + Aq1) + Aq2 = Final Emulsion (i.e. Vaccine Formulation) | | 100 |

*Concentration/Amount Ranges
Aluminum hydroxide - from about 0.0% to about 1.0% (w/v), with respect to the vaccine formulation volume
Saponin - from about 0.1 mg to about 2 mg per mL vaccine formulation
Antigens - from about 0.1 μg to about 200 μg per mL vaccine formulation
M102 & Phosphate to volume Sorbitan monooleate (SPAN 80®) and sorbitan trioleate (20 OE) (TWEEN 85®) were introduced in the oily phase. The sorbitan monooleate (20 OE) (TWEEN 80®) was not miscible in the paraffin oil. A 20% (w/v) solution of TWEEN 80® was prepared in the same buffer as the vaccine, for example, in phosphate disodic and monopotassic 0.02M isotonic buffer (pH 7.8). When the agitation stopped, the emulsion changed to an oil-in-water emulsion. The emulsion was placed in a cold chamber at 5° C. for at least 4 hours. At this stage, the emulsion was a pre-emulsion containing 50% of oily phase.

Second Step:

The aqueous phase #2 was prepared with 120 ml of phosphate disodic and monopotassic 0.02M isotonic buffer pH 7.8 with immunogens (inactivated FMDV, *Mycoplasma hyopneumoniae* immunogen, or PCV-2 immunogen, as described infra), saponin, and aluminum hydroxide. The pre-emulsion as prepared in the first step was cooled to about 5° C., diluted by adding half the volume of the aqueous phase #2 at the same temperature, and mixed by the rotation of a magnetic bar for 1 minute. Final surfactant concentration in the TSAP emulsion was 4.75% (w/v).

In general, the components of the vaccine formulations disclosed herein were added in the following order: 1) Media 102 at 5° C., 2) Saponin, 3) Alumine hydroxide, 4) Antigens, and 5) Incomplete emulsion (i.e. the combination of the Oily Phase plus the Aqueous Phase #1). As prepared herein, the TSAP vaccines are stable for up to 36 months at 5° C.

Using the same preparation method, other emulsions can be obtained as described in the prophetic examples below:

TSAP-2 Emulsion

The TSAP-2 emulsion is an O/W emulsion containing 33% of an oily phase. The oily phase (120 ml) contains MARCOL 82® 88% v/v, SPAN 80® 1.8% w/v and TWEEN 85® 10.2% w/v. The aqueous phase #1 (120 ml) contains phosphate disodic and monopotassic 0.02M isotonic buffer (pH 7.8) 97.75% v/v, and LUTROL F127® 0.75% w/v. The aqueous phase #2 (120 ml) is constituted with the phosphate disodic and monopotassic 0.02M isotonic buffer (pH 7.8), saponin, aluminum hydroxide, and optionally containing immunogens. Final surfactant concentration in the TSAP-2 emulsion is about 4.25% w/v.

TSAP-3 Emulsion

The TSAP-3 emulsion is an O/W emulsion containing 50% of an oily phase. The oily phase (160 ml) contains MARCOL 82® 92% v/v, SPAN 85® 1.8% w/v and BRIJ 96® 6.2% w/v. The aqueous phase #1 (160 ml) contains phosphate disodic and monopotassic 0.02M isotonic buffer (pH 7.8) 98.5% v/v, and LUTROL F127® 0.5% w/v, saponin, aluminum hydroxide, and optionally containing immunogens. Final surfactant concentration in the TSAP-3 emulsion is about 4.25% w/v.

TSAP-4 Emulsion

The TSAP-4 emulsion is an O/W emulsion containing 10% of an oily phase. The oily phase (120 ml) contains MARCOL 82® 60% v/v, SPAN 40® 17.2% w/v and ARLATONE 650® 22.8% w/v. The aqueous phase #1 (120 ml) contains phosphate disodic and monopotassic 0.02M isotonic buffer (pH 7.8) 97.5% v/v and TWEEN 20® 2.5% w/v. The aqueous phase #2 was prepared with 400 ml of phosphate disodic and monopotassic 0.02M isotonic buffer pH 7.8, saponin, aluminum hydroxide, and optionally containing immunogens. 100 ml of the pre-emulsion was diluted with the 400 ml of the aqueous phase #2 to obtain the TSAP-3 emulsion. Final surfactant concentration in the TSAP-4 emulsion is 4.25% w/v.

Example 2

Figure 6:
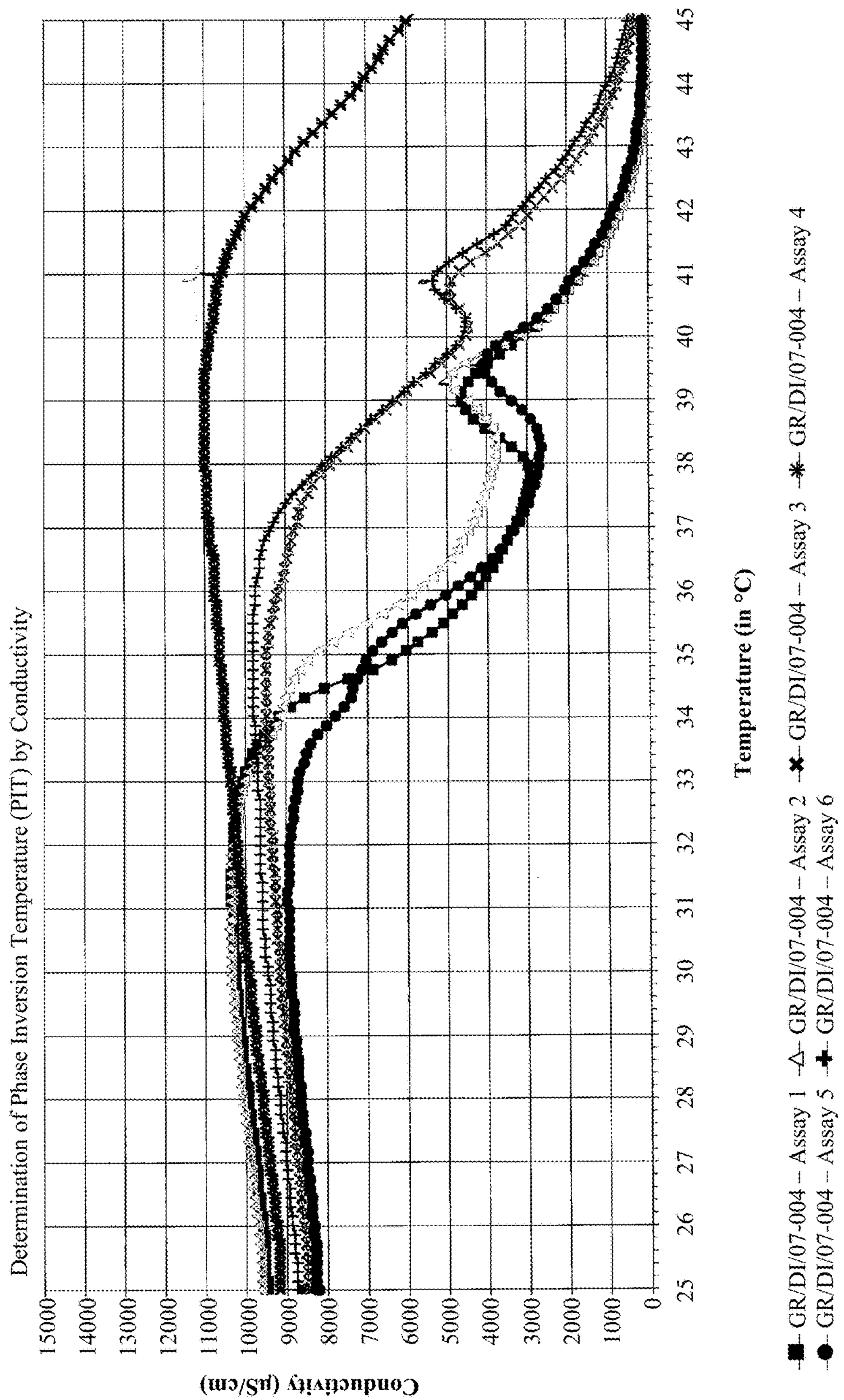
FIG. 6 provides graphs of the PIT determination for the vaccine formulations (of trials 1-9) produced according to the instant invention, and stored for 36 months.
Figure 6:
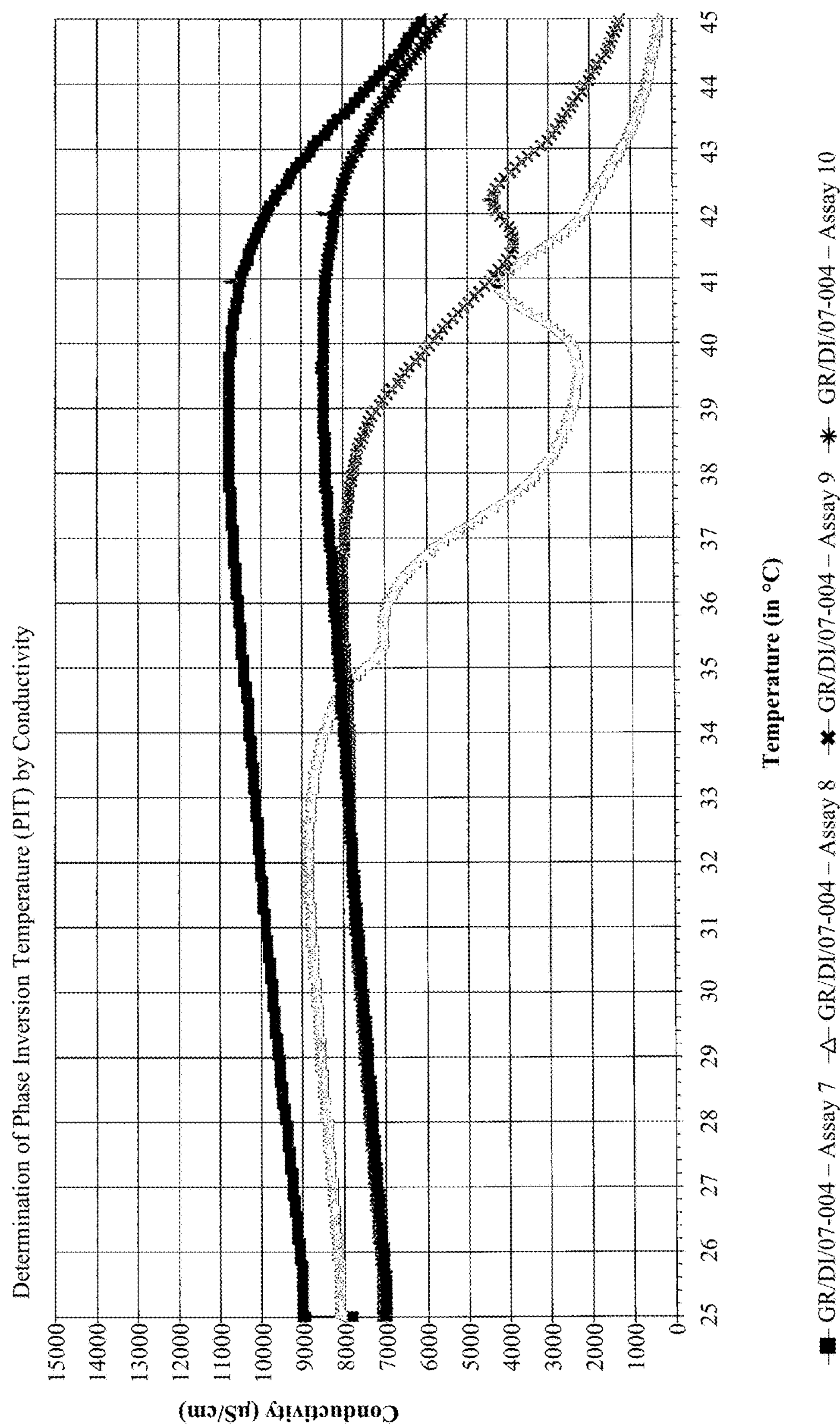
Figure 7:
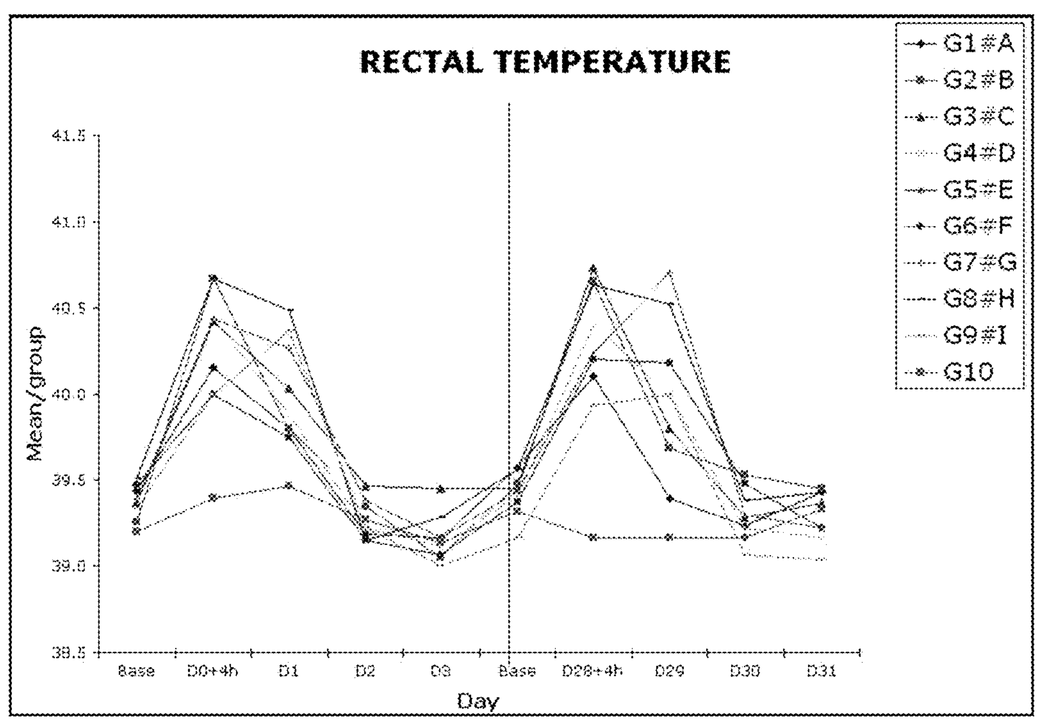
FIG. 7 provides a graph that indicates the time-dependent changes in the rectal temperature of pigs treated according to the materials and methods disclosed in Example 6.
Figure 8:
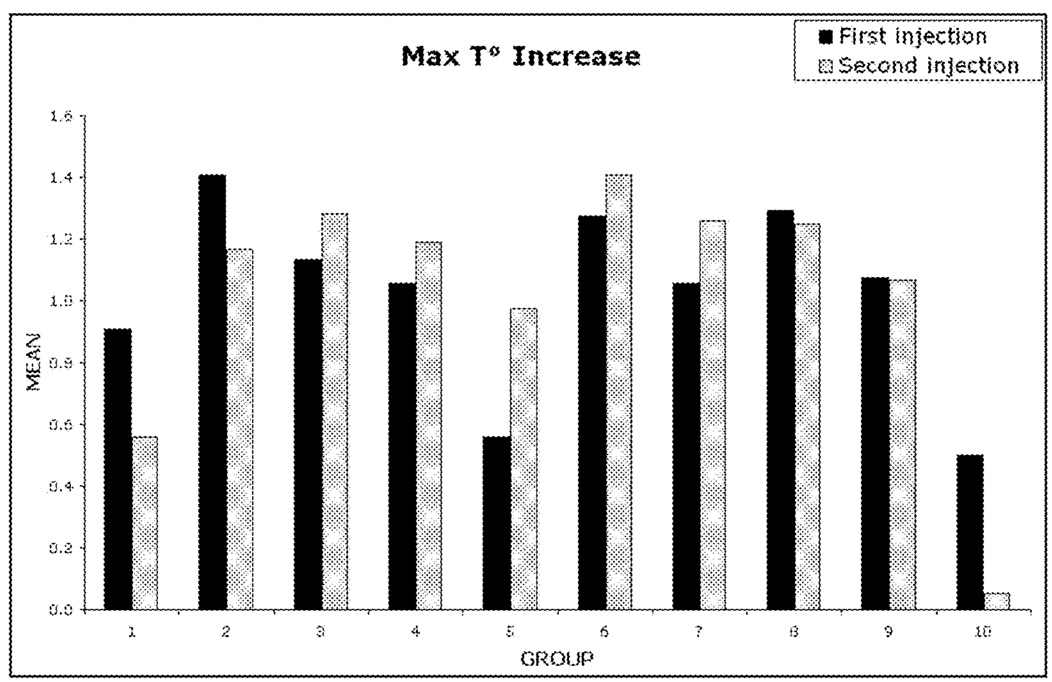
FIG. 8 provides a graph that indicates the maximum temperature change observed for pigs treated according to the materials and methods disclosed in Example 6.

Determination of the Phase Inversion Temperature (PIT) of an Emulsion 10 ml of the TSAP emulsion was placed into a glass tube in a water-bath at a temperature of about 25° C. The TSAP emulsion was a white homogeneous emulsion. The temperature in the water bath was progressively increased. Changes in the emulsion were visually observed (the emulsion became two separated phases due to the migration of the yellow-brown oily phase to the surface). This change is characteristic of the breakdown of the emulsion. The temperature at which this change is observed is the PIT value of the emulsion. For the TSAP emulsion, the PIT ranges from about 36° C.-46° C. FIGS. 1-5 provide PIT determination graphs for vaccine formulations made according to the present invention (1 year stability study). FIG. 6 provides a PIT determination graph for vaccine formulations made according to the present invention and stored for 36 months (3 year stability study).

Example 3

Study #1: Stability of Vaccine Formulations Prepared According to Example 1

This table indicates the stability (i.e. the time in months the formulations remain as oil in water emulsions) of vaccine formulations prepared according to the method described in Example 1. The formulations are comprised of the indicated constituent ingredients (see formulations 1-13), and the antigens used for each of these formulations comprised inactivated FMD virus isolates that were considered moderately to highly purified.

As Table 2 indicates, the presence of Aluminum hydroxide provides increased vaccine stability especially when the highest concentration of antigen is used (compare the enhanced stability of formulations 9, 11, and 13 to the relatively reduced stability at 12 months of formulations 3, 5, and 7). On average, the presence of Aluminum hydroxide in the higher antigen-containing formulations (i.e. formulations 9, 11, and 13) increases the oil/water stability time from about 3-6 months (i.e. the oil/water stability observed for formulations 3, 5, and 7) to about twelve (12) months (i.e. the oil/water stability observed for formulations 9, 11), or even to about twenty four (24) months (i.e. the oil/water stability observed for formulation 13).

TABLE 4-continued

| Component Description | For 1 L of M102 | Stock Solution |
|---|---|---|
| $CHCl_3$ | 5 ml | pure |
| Alanine | 276 g | — |
| Glucose | 1880 | 4500 mM |
| Sodium Bicarbonate | 2180 | 2540 mM |
| Peptone | 3000 g | — |
| Lactalbumin hydrolysate | 4000 g | — |

TABLE 2

| Trial | 1 | 2 | 3 | 4 | 5 | 6 | 7 | 8 | 9 | 10 | 11 | 12 | 13 |
|---|---|---|---|---|---|---|---|---|---|---|---|---|---|
| Antigen (μg/dose) | 0 | 15 | 60 | 15 | 60 | 15 | 60 | 15 | 60 | 15 | 60 | 15 | 60 |
| Saponin (mg/dose) | 0 | 0 | 0 | 0.5 | 0.5 | 1 | 1 | 0 | 0 | 0.5 | 0.5 | 1 | 1 |
| $Al(OH)_3$ (% final) | 0 | 0 | 0 | 0 | 0 | 0 | 0 | 0 | .3 | .3 | .3 | .3 | .3 |
| Number doses | 75 | 75 | 75 | 75 | 75 | 75 | 75 | 75 | 75 | 75 | 75 | 75 | 75 |
| T0 Mos | O/W | O/W | O/W | O/W | O/W | O/W | O/W | O/W | O/W | O/W | O/W | O/W | O/W |
| T3 Mos | O/W | O/W | O/W | O/W | O/W | O/W | O/W | O/W | O/W | O/W | O/W | O/W | O/W |
| T6 Mos | O/W | O/W | W/O | O/W | W/O | O/W | O/W | O/W | O/W | O/W | O/W | O/W | O/W |
| T9 Mos | O/W | O/W | W/O | O/W | W/O | O/W | W/O | O/W | O/W | O/W | O/W | O/W | O/W |
| T12 Mos | O/W | O/W | W/O | O/W | W/O | O/W | W/O | O/W | O/W | O/W | O/W | O/W | O/W |
| T24 Mos | O/W | O/W | W/O | O/W | W/O | OW/ | W/O | O/W | W/O | O/W | W/O | O/W | O/W |

Example 4

Study #2: Stability of Vaccine Formulations Prepared According to Example 1

Vaccine formulations were prepared as described in Example 1 and according to the component amounts indicated in Table 3. As described previously, the order of addition of components was 1) media 102, 2) saponin, 3) alumine hydroxide, 4) purified antigens, and 5) incomplete emulsion (refer to Example 1 wherein the incomplete emulsion is defined as the oily phase plus the aqueous phase #1). The purified antigens were FMDV antigens O1 Campos, A24 Cruzeiro, and C3 Indaial. The total volume was adjusted using Media 102 (M102, recipe indicated below).

Vaccine stability was determined according to Table 5.

TABLE 5

| Test | Acceptability criteria |
|---|---|
| Droplet size analysis** | Mode < 0.18 μm; SPAN < 0.8* |
| Phase inversion temperature (PIT) | >=36° C. |

*For the vaccines without alumine gel

**Controls performed at the end of the stability study

For each vaccine formulation, the phase inversion temperature (PIT) was determined as described in Example 2. The amount of antigen added is indicated by "hemagluttinin units" (UH) per vaccine dose. Table 6 summarizes the PIT data and indicates that the PIT remained generally stable for up to 36 months. FIG. 6 provides graphs of the PIT determination by conductivity for the vaccine formulations of Trials 1-10 (summarized in Table 6). The increase of the PIT that is observed with the saponin-adjuvanted formulations (i.e. trials 3, 4, 6, 7, 9, and 10) constitutes by itself an improvement with respect to stability over non-saponin-adjuvanted formulations (i.e. trials 2, 5, and 8).

TABLE 3

| Trial Number | 1 | 2 | 3 | 4 | 5 | 6 | 7 | 8 | 9 | 10 |
|---|---|---|---|---|---|---|---|---|---|---|
| Incomplete emulsion (ml) | 400 | 400 | 400 | 400 | 400 | 400 | 400 | 400 | 400 | 400 |
| Aqueous phase (ml) | 200 | 200 | 200 | 200 | 200 | 200 | 200 | 200 | 200 | 200 |
| saponin 4MIL1R159B (mg) | 0 | 0 | 250 | 9570 | 0 | 250 | 9570 | 0 | 250 | 9570 |
| O1(ml) [about 1500 μg] | 0 | 18.8 | 18.8 | 18.8 | 18.8 | 18.8 | 18.8 | 18.8 | 18.8 | 18.8 |
| A24 (ml) [about 1500 μg] | 0 | 16.7 | 16.7 | 16.7 | 16.7 | 16.7 | 16.7 | 16.7 | 16.7 | 16.7 |
| C3 (ml) [about 1500 μg] | 0 | 15 | 15 | 15 | 15 | 15 | 15 | 15 | 15 | 15 |
| Alumine hydroxide 1.5% (ml) | 0 | 0 | 0 | 0 | 25 | 25 | 25 | 150 | 150 | 150 |
| Media 102 | QSP 200 ml | | | | | | | | | |
| Total volume (ml) | 600 | 600 | 600 | 600 | 600 | 600 | 600 | 600 | 600 | 600 |
| Total volume (doses) | 300 | 300 | 300 | 300 | 300 | 300 | 300 | 300 | 300 | 300 |

TABLE 4

| Component Description | For 1 L of M102 | Stock Solution |
|---|---|---|
| $MgCl_2$ | 95 | 170 mM |
| KCl | 190 | 400 mM |
| $CaCl_2$ | 238 | 260 mM |

TABLE 6

| Trials | 1 | 2 | 3 | 4 | 5 | 6 | 7 | 8 | 9 | 10 |
|---|---|---|---|---|---|---|---|---|---|---|
| Days | 7 | 7 | 7 | 8 | 7 | 9 | 9 | 9 | 14 | 14 |
| | 22 | 22 | 23 | 23 | 24 | 24 | 29 | 38 | 38 | 41 |
| | 121 | 121 | 121 | 122 | 121 | 121 | 127 | 123 | 133 | 133 |
| | 330 | 330 | 330 | 340 | 340 | 340 | 340 | 340 | 340 | 340 |
| | 1100 | 1100 | 1100 | 1100 | 1100 | 1100 | 1100 | 1100 | 1100 | 1100 |
| Antigen | − | + | + | + | + | + | + | + | + | + |
| Saponin (mg/dose) | 0 | 0 | 0.8 | 2.5 | 0 | 0.8 | 2.5 | 0 | 0.8 | 2.5 |
| Alumine gel (%) | 0 | 0 | 0 | 0 | 0.065 | 0.065 | 0.065 | 0.39 | 0.39 | 0.39 |
| P.I.T. | 39 | 36 | 39 | 39.5 | 36 | 39 | 39.5 | 37.5 | 40 | 40 |
| | 32.5(*) | 36.5 | 39 | 40 | 36.5 | 39 | 39.5 | 37.5 | 39.5 | 40.5 |
| | 35 | 36.5 | 36.7(*) | 39.5 | 37 | 39 | 40 | 32(*) | 40 | 40.5 |
| | 36.5 | 37 | 39 | 39 | 37 | 39 | 39 | 38 | 40 | 39.5 |
| | 38.5 | 39.0 | 40.5 | 40 | 39 | 40.5 | 40 | 41 | 41.5 | 40.5 |

The particle size distribution (Table 7) of the emulsions remained within the range set forth in the study criteria over the 36 month time period.

TABLE 7

| Samples | Date of manufacturing | Date of analysis | Ag (+/−) | Saponin (mg/dose) | Alumine gel (% final) | Mode (μm) | SPAN |
|---|---|---|---|---|---|---|---|
| Incomplete emulsion | 4 Jul. 2005 | 5 Jul. 2005 | − | 0 | 0 | 0.158 | 0.644 |
| Trial 1 | 27 Sep. 2005 | 4 Dec. 2009 | − | 0 | 0 | 0.146 | 0.650 |
| Trial 2 | 27 Sep. 2005 | 4 Dec. 2009 | + | 0 | 0 | 0.145 | 0.661 |
| Trial 3 | 27 Sep. 2005 | 4 Dec. 2009 | + | 0.8 | 0 | 0.148 | 0.633 |
| Trial 4 | 27 Sep. 2005 | 4 Dec. 2009 | + | 2.5 | 0 | 0.154 | 0.582 |
| Trial 5 | 27 Sep. 2005 | 4 Dec. 2009 | + | 0 | 0.065 | 0.144 | 0.670 |
| Trial 6 | 27 Sep. 2005 | 4 Dec. 2009 | + | 0.8 | 0.065 | 0.144 | 0.672 |
| Trial 7 | 27 Sep. 2005 | 4 Dec. 2009 | + | 2.5 | 0.065 | 0.144 | 0.672 |
| Trial 8 | 27 Sep. 2005 | 5 Dec. 2009 | + | 0 | 0.39 | 0.146 | 0.790 |
| Trial 9 | 27 Sep. 2005 | 5 Dec. 2009 | + | 0.8 | 0.39 | 0.145 | 0.789 |
| Trial 10 | 27 Sep. 2005 | 5 Dec. 2009 | + | 2.5 | 0.39 | 0.145 | 0.787 |

Example 5

Serology Results after Administration of Multiple Doses of a Foot-and-Mouth Disease (FMD) Virus Vaccine Adjuvanted with TSAP Emulsion—Bovine Study Materials and Methods: 90 Cattle, 12 to 14 months old, never vaccinated, and without FMD antibodies were selected, randomized, and distributed among 10 groups of 9 animals to be vaccinated. The animals were vaccinated with the indicated vaccine formulations (9807-9814) at day 1. Each of the formulations listed in Tables 8, 9, 10, and 11 was prepared according to Example 1 and comprises all the components recited in Example 1 with the saponin and aluminum hydroxide amounts varying according to the following: the amount of saponin is either 0, 0.7, 1.3, or 2.7 mg/dose, and the amount of Algel aluminum hydroxide is either 0% or 0.37%. Eight (8) groups were vaccinated by the intramuscular route (the IM group) and two (2) groups were vaccinated by the subcutaneous route (the SC group). Each animal of the IM group was revaccinated with the respective vaccine on day 56 by the intramuscular route and on day 84 by the subcutaneous route. Each animal of the SC group was revaccinated with the respective vaccine on days 56 and 84 by the subcutaneous route.

Table 8 summarizes the stability of the vaccine formulations.

TABLE 8

| Formulation | 6° C. | | | Environment | | |
|---|---|---|---|---|---|---|
| Number | 1 Week | 2 Weeks | 30 Days | 1 Week | 2 Weeks | 30 Days |
| 9807 | OK | OK | OK | OK | OK | OK |
| 9808 | OK | OK | OK | OK | OK | OK |
| 9809 | OK | OK | OK | OK | OK | OK |
| 9810 | OK | OK | OK | OK | OK | OK |
| 9811 | OK | OK | OK | OK | OK | OK |
| 9812 | OK | OK | OK | OK | OK | OK |
| 9813 | OK | OK | OK | OK | OK | OK |
| 9814 | OK | OK | OK | OK | OK | OK |

There was not any lesion after the first vaccination by the intramuscular route. There were some lesions after the second vaccination by the intramuscular route but all these lesions receded 28 days after the second vaccination by the intramuscular route. Table 9 summarizes the safety of the vaccine formulations, as indicated by animal body weight measurement on the specified dates.

TABLE 9

| Experiment Identifier | Statistics | 17 Nov. 2008 | 8 Dec. 2008 | 15 Dec. 2008 | 12 Jan. 2009 | 15 Jan. 2009 | 9 Feb. 2009 | 12 Feb. 2009 | 16 Feb. 2009 | 9 Mar. 2009 |
|---|---|---|---|---|---|---|---|---|---|---|
| | | Body Weight Measurement Date | | | | | | | | |
| EXP 9807 | Mean Wt (kg) | 294 | 303 | 305 | 331 | 330 | 354 | 352 | 355 | 372 |
| | StdDev | 33 | 30 | 31 | 35 | 33 | 34 | 34 | 32 | 37 |
| EXP 9808 | Mean Wt (kg) | 293 | 304 | 305 | 331 | 328 | 352 | 355 | 354 | 370 |
| | StdDev | 34 | 36 | 35 | 35 | 41 | 39 | 42 | 41 | 42 |
| EXP 9809 | Mean Wt (kg) | 293 | 304 | 304 | 327 | 325 | 351 | 345 | 348 | 365 |
| | StdDev | 33 | 33 | 32 | 29 | 33 | 29 | 37 | 35 | 37 |
| EXP 9810 | Mean Wt (kg) | 293 | 305 | 307 | 330 | 330 | 350 | 348 | 351 | 374 |
| | StdDev | 33 | 32 | 30 | 39 | 36 | 37 | 34 | 34 | 40 |
| EXP 9811 G1 | Mean Wt (kg) | 295 | 307 | 307 | 328 | 329 | 352 | 346 | 352 | 369 |
| | StdDev | 34 | 31 | 31 | 31 | 34 | 36 | 35 | 40 | 39 |
| EXP 9811 G2 | Mean Wt (kg) | 293 | 304 | 305 | 328 | 329 | 346 | 342 | 345 | 364 |
| | StdDev | 31 | 32 | 34 | 34 | 37 | 41 | 39 | 41 | 43 |
| EXP 9812 G1 | Mean Wt (kg) | 294 | 307 | 307 | 329 | 331 | 352 | 350 | 354 | 371 |
| | StdDev | 29 | 33 | 34 | 35 | 35 | 37 | 36 | 35 | 32 |
| EXP 9812 G2 | Mean Wt (kg) | 292 | 304 | 304 | 330 | 329 | 352 | 349 | 355 | 369 |
| | StdDev | 30 | 32 | 32 | 34 | 37 | 35 | 32 | 37 | 33 |
| EXP 9813 | Mean Wt (kg) | 293 | 304 | 304 | 332 | 331 | 357 | 354 | 360 | 378 |
| | StdDev | 30 | 27 | 27 | 28 | 30 | 33 | 30 | 30 | 35 |
| EXP 9814 | Mean Wt (kg) | 293 | 304 | 305 | 327 | 325 | 348 | 343 | 346 | 365 |
| | StdDev | 30 | 31 | 29 | 31 | 30 | 32 | 35 | 31 | 29 |

Results: Table 10 summarizes the serological data collected during the experimental trials. O1 Campos, A24 Cruzeiro, and C3 Indaial are three independent serotypes of the FMD virus, and the presence of O1, A24, and C3 antibodies is a positive indicator that the vaccine formulation elicited an immune response in the vaccinates. "G1" indicates the vaccine formulation was administered intramuscularly and "G2" indicates the vaccine formulation was administered subcutaneously. For the present invention, particularly for the FMD viral antigens, there is a strong, direct correlation between antibody titer (i.e. serum levels of O1 Campos, A24 Cruzeiro, and C3 Indaial) and the Equivalent Population Protection (EPP) number. Simply stated, when the antibody titers are high, the vaccinate animals are correspondingly highly protected from viral infection.

Surprisingly, the presence of aluminum hydroxide is associated with a significant difference in immune response that depends upon the route of administration. When aluminum hydroxide is present, as in formulations 9812G1 and 9812G2, there is a significant increase in the vaccinate immune response, as measured by the antibody titers, when the vaccine formulation is administered subcutaneously. There is no similar significant difference in efficacy due to route of administration for the corresponding vaccine formulations that do not contain aluminum hydroxide, namely 9811G1 and 9811G2.

The reason for this enhanced immune response due to the presence of aluminum hydroxide coincident with the use of the subcutaneous route of administration is not known at this time, but an effective embodiment of the current invention could include, but is in no way limited to, varying the route of vaccine administration dependent upon current and future efficacy (e.g. antibody titer) data.

As compared to non-saponin-adjuvanted control vaccine formulations (i.e. 9807 & 9808), the saponin-adjuvanted vaccine formulations elicit in the study animals a more rapid immune response to all three FMD virus antigens, as indicated by the higher average antibody titers for saponin-adjuvanted formulations at Day 21. Taken together, the evidence indicates that the present invention provides improved stability and enables more rapid immune responses than non-saponin adjuvanted formulations.

TABLE 10

| | | | O1 CAMPOS | | | | A24 CRUZEIRO | | | | C3 INDAIAL | | | | MEANS | |
|---|---|---|---|---|---|---|---|---|---|---|---|---|---|---|---|---|
| Saponin | $Al(OH)_3$ | | D21 | | D56 | | D21 | | D56 | | D21 | | D56 | | D21 | D56 |
| (mg/dose | (%) | Form. ID | TIT | EPP | TIT | EPP | TIT | EPP | TIT | EPP | TIT | EPP | TIT | EPP | TIT | TIT |
| 0 | 0 | 9807 | 1.47 | 37.7 | 2.07 | 80.4 | 1.56 | 29.4 | 2.01 | 71.6 | 1.97 | 69.5 | 2.41 | 92.3 | 1.67 | 2.2 |
| 0 | 0.37 | 9808 | 1.64 | 51.3 | 1.59 | 45.6 | 1.9 | 55.1 | 1.66 | 30.5 | 2.08 | 77.3 | 2.14 | 85.8 | 1.88 | 1.8 |
| 0.7 | 0 | 9809 | 1.66 | 49.4 | 1.91 | 64.9 | 1.97 | 61.5 | 1.9 | 52.8 | 2.05 | 77.4 | 2.37 | 87.7 | 1.89 | 2.1 |
| 0.7 | 0.37 | 9810 | 1.91 | 71.3 | 1.82 | 64.5 | 2.02 | 65.7 | 1.81 | 46.9 | 2.27 | 88.7 | 2.28 | 88 | 2.07 | 2 |
| 1.3 | 0 | 9811 G1 | 1.97 | 74.6 | 2.18 | 82.6 | 2.03 | 67.8 | 2.01 | 70.1 | 2.32 | 88.6 | 2.46 | 92.2 | 2.11 | 2.2 |
| 1.3 | 0 | 9811 G2 | 1.92 | 73.4 | 2.06 | 84 | 2.05 | 68.2 | 2.11 | 74 | 2.33 | 92.2 | 2.55 | 95.3 | 2.1 | 2.2 |
| 1.3 | 0.37 | 9812 G1 | 1.81 | 62.5 | 1.98 | 67.3 | 2.08 | 73.4 | 1.88 | 49.2 | 2.29 | 88.5 | 2.27 | 87.4 | 2.06 | 2 |
| 1.3 | 0.37 | 9812 G2 | 2.58 | 98.9 | 2.42 | 97 | 2.5 | 94.5 | 2.29 | 90 | 2.59 | 96.7 | 2.76 | 98.8 | 2.56 | 2.5 |
| 2.7 | 0 | 9813 | 2 | 79.5 | 2.31 | 93.5 | 2.22 | 87.5 | 2.23 | 88.6 | 2.43 | 93.4 | 2.69 | 96.5 | 2.22 | 2.4 |
| 2.7 | 0.37 | 9814 | 2.14 | 88.2 | 2.03 | 80.2 | 2.34 | 95.1 | 1.96 | 57.4 | 2.6 | 96.4 | 2.39 | 92.5 | 2.36 | 2.1 |

G1 - vaccine formulation was administered intramuscularly

G2 - vaccine formulation was administered subcutaneously

Example 6

Serology Results after Administration of Two Doses of a Foot-and-Mouth Disease (FMD) Virus Vaccine Adjuvanted with TSAP Emulsion—Porcine Study Materials and Methods: 57 Pigs, never vaccinated, and without FMD antibodies were selected, randomized, and distributed among 9 groups of 6 animals to be vaccinated and 1 group of 3 animals not to be vaccinated (non-vaccinated animals). The animals were vaccinated with either the indicated vaccine formulations (A-I) on day 1. Each of the formulations listed in Table 11 was prepared according to Example 1 and comprises all the components recited in Example 1 with the saponin and aluminum hydroxide varying according to the following: the amount of saponin is either 0, 0.7, 1.3, or 2.7 mg/dose and the amount of Algel aluminum hydroxide is either 0% or 0.37%. Vaccine formulation safety was assessed via measurement of several parameters including rectal temperature and visual indicia of the animal's reaction to vaccination.

TABLE 11

| | Vaccine Formulation | | | | | | | | |
|---|---|---|---|---|---|---|---|---|---|
| | A | B | C | D | E | F | G | H | I |
| Ag (μg/dose) | 0 | 10 | 10 | 10 | 10 | 10 | 10 | 10 | 10 |
| Saponin (mg/dose) | 0 | 0 | 0 | 0.7 | 0.7 | 1.3 | 1.3 | 2.7 | 2.7 |
| Algel (% final) | 0 | 0 | 0.37 | 0 | 0.37 | 0 | 0.37 | 0 | 0.37 |
| Incomplete Emulsion | 333 | 333 | 333 | 333 | 333 | 333 | 333 | 333 | 333 |
| Aqueous Phase 2 (166 mL) | | | | | | | | | |
| Purified FMDV (mL) | 0 | 11.1 | 11.1 | 11.1 | 11.1 | 11.1 | 11.1 | 11.1 | 11.1 |
| Saponin (mL) | 0 | 0 | 0 | 2.48 | 2.48 | 4.96 | 4.96 | 9.92 | 9.92 |
| Algel 3% (mL) | 0 | 0 | 61.7 | 0 | 61.7 | 0 | 61.7 | 0 | 67.7 |
| M102 at 5° C. | 166 | 154.9 | 93.2 | 152.4 | 90.8 | 149.9 | 88.2 | 145 | 83.3 |
| Total | | | | | | | | | |
| Volume total (mL) | 500 | 500 | 500 | 500 | 500 | 500 | 500 | 500 | 500 |
| Number total (doses) | 250 | 250 | 250 | 250 | 250 | 250 | 250 | 250 | 250 |

Results: All vaccine formulations that contained antigen (formulations B-I, described in Table 11) induced in the test animals an antibody response that was significantly greater than that induced by the no antigen control (formulation I, described in Table 11). Formulations that contained saponin induced relatively greater antibody responses as compared to formulations that contained no saponin. Table 12 summarizes the antibody titer data, and restates the amounts of antigen, saponin, and aluminum hydroxide for each formulation. In particular, the antibody titer data indicates that the presence in vaccine formulations of between about 0.7 mg/dose and about 2.7 mg/dose saponin increases the antibody response, relative to vaccine formulations that do not contain saponin.

TABLE 12

| Animal Group | Vaccine Formulation | Antigen (μg/dose) | Saponin (mg/dose) | Algel | Average Antibody Titer Data Statistic | D 21 | D 44 |
|---|---|---|---|---|---|---|---|
| G1 | A | 0 | 0 | 0 | Mean | 0.75 | 0.67 |
| | | | | | StdDev | 0.26 | 0.26 |
| G2 | B | 10 | 0 | 0 | Mean | 1.45 | 3.17 |
| | | | | | StdDev | 0.50 | 0.48 |
| G3 | C | 10 | 0 | 0.37 | Mean | 1.40 | 2.92 |
| | | | | | StdDev | 0.18 | 0.31 |
| G4 | D | 10 | 0.7 | 0 | Mean | 1.60 | 3.12 |
| | | | | | StdDev | 0.31 | 0.42 |
| G5 | E | 10 | 0.7 | 0.37 | Mean | 1.87 | 3.20 |
| | | | | | StdDev | 0.69 | 0.45 |
| G6 | F | 10 | 1.3 | 0 | Mean | 1.40 | 3.41 |
| | | | | | StdDev | 0.37 | 0.27 |
| G7 | G | 10 | 1.3 | 0.37 | Mean | 1.80 | 3.37 |
| | | | | | StdDev | 0.22 | 0.43 |
| G8 | H | 10 | 2.7 | 0 | Mean | 1.72 | 3.47 |
| | | | | | StdDev | 0.66 | 0.30 |

TABLE 12-continued

| Animal Group | Vaccine Formulation | Antigen (μg/dose) | Saponin (mg/dose) | Algel | Average Antibody Titer Data Statistic | D 21 | D 44 |
|---|---|---|---|---|---|---|---|
| G9 | I | 10 | 2.7 | 0.37 | Mean | 1.47 | 2.97 |
| | | | | | StdDev | 0.18 | 0.57 |
| G10 | Not Vaccinated | — | — | — | Mean | 0.67 | 0.67 |
| | | | | | StdDev | 0.17 | 0.09 |

Example 7

Determination of the Protective Dose 50% (PD50) of Three Experimental FMD Vaccines in Pigs Overview.

The purpose of the study was to test the efficacy against FMD virulent challenge in pigs of 3 experimental FMD vaccine formulations according to the instant invention. Four vaccines (A, B, C, and D) were prepared with respectively no Antigen (A), and variable doses of inactivated purified FMD O1 Manisa antigen (vaccines B, C, and D) formulated with adjuvant according to the instant invention. The vaccines were presented as 30 mL vials filled to 25 mL and the doses were 2 mL per dose. The challenge strain was FMD O1 Manisa, 449402 4D:911, Jul. 20, 1994 (which had been originally isolated as O1 Manisa Turkey 1/78), and the titer in secondary porcine kidney cells was 7.67 log 10 TCID50/mL. Diluent for the challenge strain was Hanks MEM, 2% fetal bovine serum (FBS) with standard antibiotics.

Procedure.

Porcines free from FMDV and not previously vaccinated against FMD were used for the study. Each of 47 pigs aged 10 weeks (plus or minus 1 week) was acclimatized for at least 24 hours prior to experimental procedures. Pigs were housed 2 to 3 animals per room, and were fed standard pellet feed and watered ad libitum. At Day 1 (D1), the pigs (regardless of sex) were allocated to 15 groups of three animals and one group of two animals. Each group was housed in one particular room and in each room, the animals were individually separated by wooden planks (1.5M) from challenge until completion of the study.

On D0, animals were vaccinated, intramuscularly behind the ear on the left side, with individual syringes according to Tables 13 and 14. Before vaccination, vaccine vials were gently inverted about 10 times to ensure homogeneous suspension.

TABLE 13

| vaccine composition | | | | |
|---|---|---|---|---|
| Vaccine (Final Emulsion) | A | B | C | D |
| Ag (μg/dose) | 0 | 0.4 | 2 | 10 |
| Saponin (mg/dose) | 0 | 0 | 0 | 0.7 |
| Algel (% final) | 0 | 0.42 | 0.42 | 0.42 |
| Incomplete Emulsion (ml) | 333 | 333 | 333 | 333 |
| Aqueous phase 2 166 ml | | | | |
| FMD O-Manisa batch# OMAd-04-613 (ml) | 0 | 0.66 | 3.29 | 16.46 |
| Pure Saponin 08-0314-P (ml) | 0 | 2.48 | 2.48 | 2.48 |
| Alumine Gel 3% (ml) | 0 | 61.4 | 61.4 | 61.4 |
| Media 102 | 166 | 102.5 | 99.8 | 86.7 |

TABLE 13-continued

| vaccine composition | | | | |
|---|---|---|---|---|
| Vaccine (Final Emulsion) | A | B | C | D |
| Total | | | | |
| Volume total (ml) | 500 | 500 | 500 | 500 |
| # total (doses) | 250 | 250 | 250 | 250 |

TABLE 14 vaccination summary

| Group | Vaccine | Dose | Volume of Vaccine Injected (mL) | # Pigs |
|---|---|---|---|---|
| B1 | B | Dose | 2.0 | 3 |
| B2 | B | ½ dose | 1 | 3 |
| B3 | B | ¼ dose | 0.5 | 3 |
| B4 | B | ⅛ dose | 0.25 | 3 |
| B5 | B | 1/16 dose | 0.13 | 3 |
| C1 | C | Dose | 2.0 | 3 |
| C2 | C | ½ dose | 1 | 3 |
| C3 | C | ¼ dose | 0.5 | 3 |
| C4 | C | ⅛ dose | 0.25 | 3 |
| C5 | C | 1/16 dose | 0.13 | 3 |
| D1 | D | Dose | 2.0 | 3 |
| D2 | D | ½ dose | 1 | 3 |
| D3 | D | ¼ dose | 0.5 | 3 |
| D4 | D | ⅛ dose | 0.25 | 3 |
| D5 | D | 1/16 dose | 0.13 | 3 |
| A (control) | A | 1 | 2 | 2 |

Challenge.

On D28, FMD type O virus was diluted to obtain 100,000 TCID50 per mL (the virus stock was diluted 2.67 log 10, or 468 times). On the same day, all animals were anesthetized by administration of STRESSNIL (1 mL/20 kg) and KETAMINE (2 mL/20 kg) by the IM route and challenged with 10,000 TCID50 of virus under 0.1 mL by intra-dermal route, into the bulb of the heel of the outer claw of the left hind foot. The general well being of the animals was checked daily from D0 to D28. Any clinical observations and treatments were noted. After challenge, animals were observed daily for 7 day (D29 to D35). Observations were performed in the same order, starting by the rooms with the animals vaccinated with the highest to dose to those with the animals vaccinated with the lowest dose, and ending with the controls (group A). The general well being was checked daily, with particular attention paid to signs of FMD on the snoot and the feet. Blood was collected from each animal before vaccination (on D1 or D0), D14, and D28 before challenge and at the end of the study. Samples were heat-inactivated (56° C. for 30 minutes) and FMDV Ab type O titer was determined in all sera by VN test (MERIAL R&D, Lelystad).

On D36 (end of the observation period), animals were euthanized (4 to 6 mL per 50 kg IV T61) and closely inspected for signs of FMDV. Any lesions observed in the groups vaccinated with a full dose of vaccine (groups B1, C1, or D1) were samples and frozen at −70° C. for further virus typing. Presence of lesions on the snoot, mouth and/or feet (except on the major claw of the inoculated feet) were considered as an evidence of FMD. The test was considered valid as it met the criteria, which stated both control pigs must show FMD clinical signs. The PD50 of each vaccine was calculated by Spearman Karber method.

Results.

Figure 9:
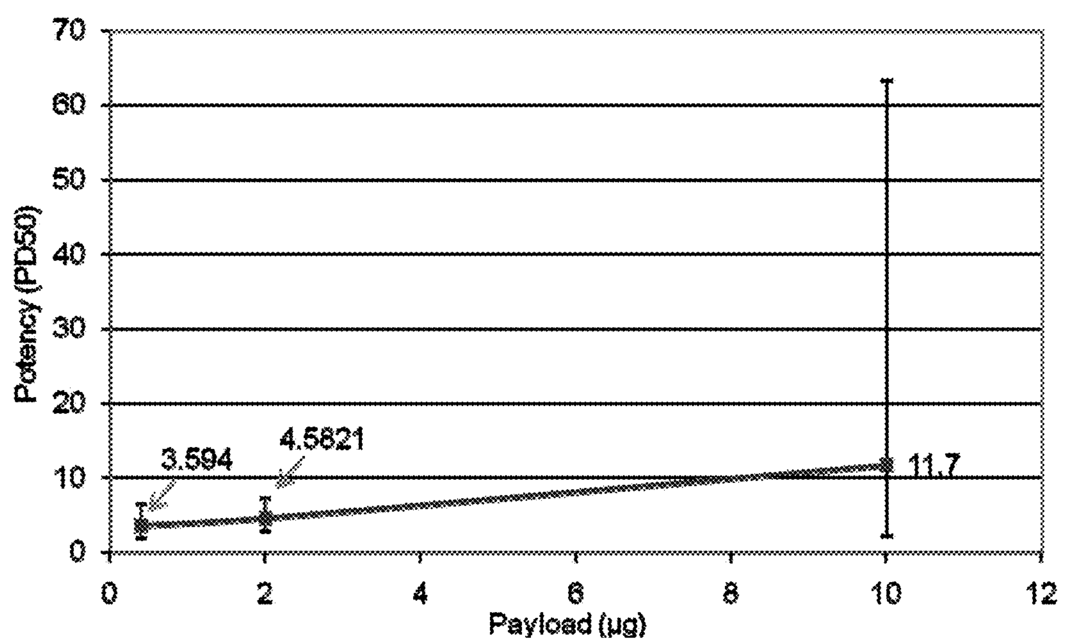
FIG. 9 provides a graph that indicates vaccine potency (PD50) versus payload (μg) for pigs treated according to the materials and methods disclosed in Example 7.

The potency versus payload is presented in FIG. 9, and the relevant study data is numerically summarized in Tables 15 and 16 below.

TABLE 15

| Volume | # protected pigs per vaccine tested | | |
|---|---|---|---|
| (ml) | B | C | D |
| 2.000 | 3/3 | 2/2 | 3/3 |
| 1.000 | 2/3 | 3/3 | 3/3 |
| 0.500 | 1/3 | 1/3 | 3/3 |
| 0.250 | 1/3 | 1/3 | 2/3 |
| 0.125 | 0/3 | 0/3 | 1/3 |

TABLE 16

| Calculation of vaccine potency using logistic regression | | | | |
|---|---|---|---|---|
| Vaccine | Payload (μg) | PD50 | IC95− | IC95+ |
| B | 0.4 | 3.594 | 1.6046 | 2.896 |
| C | 2 | 4.5821 | 1.7021 | 2.6979 |
| D | 10 | 11.7 | 9.533 | 51.55 |

What is claimed is:

1. A safe and effective stable injectable oil-in-water (O/W) vaccine emulsion, wherein the emulsion is effective for eliciting a protective immunologic response in a porcine vaccinate, comprising:

(i) at least about 10 μg of antigen/2 mL vaccine dose, wherein the antigen is foot and mouth disease virus (FMDV), dissolved in the aqueous phase of the emulsion;

(ii) 0.7 to about 1.3 mg/2 mL vaccine dose of a saponin, dissolved in the aqueous phase of the emulsion; wherein the saponin consists of an anion-exchange column purified extract of *Quillaja saponaria* Molina bark enriched for QS-17, QS-18 and QS-21;

(iii) about 0.37% to about 0.42% w/v (of the emulsion) aluminum hydroxide, dissolved in the aqueous phase of the emulsion;

(iv) a mineral oil, present in an amount of about 20% to about 40% of the emulsion;

(v) a non-ionic lipophilic surfactant, present in the amount of 0.1% to about 2.5% w/v of the emulsion, and selected from sorbitan fatty acid monoesters, fatty acid esters of mannide, ethoxylated fatty acid esters of mannide, and combinations thereof;

(vi) a non-ionic hydrophilic surfactant, present in the amount of 0.1% to about 1.5% w/v of the emulsion, and having a high hydrophilic-lipophilic balance (HLB) value between 13 and 40 selected from ethoxylated fatty acid monoesters of sorbitan, ethoxylated fatty acids, and combinations thereof; and (vii) a non-ionic hydrophilic surfactant present, in the amount of about 1% to about 8% w/v of the emulsion, and having a low hydrophilic-lipophilic balance (HLB) value between 9 and 13 selected from ethoxylated fatty acid triesters of sorbitan, ethoxylated fatty acid diesters of sorbitan, ethoxylated fatty acid monoesters of sorbitan, ethoxylated fatty acids, ethoxylated castor oil and, combinations thereof;

wherein the final HLB of the emulsion is from about 9 to about 12; and wherein the emulsion remains a stable O/W emulsion for at least 24 months; and wherein the only oil present in the emulsion is the mineral oil.

2. The emulsion of claim 1, wherein the concentration of the aluminum hydroxide is about 0.42% (w/v).

3. The emulsion of claim 1, wherein the amount of antigen is at least about 60 μg per 2 mL vaccine dose.

4. The emulsion of claim 1, wherein the amount of saponin is 0.7 mg/dose.

5. The emulsion of claim 1, wherein the amount of saponin is about 1.3 mg/2 mL vaccine dose.

6. The emulsion of claim 1, wherein the antigen further comprises a bacterial antigen.

7. The emulsion of claim 1, wherein the antigen consists essentially of a combination of an FMDV antigen, a PCV2 antigen and a bacterial antigen.

8. The emulsion of claim 1, wherein the high HLB non-ionic hydrophilic surfactant is present at a concentration of 0.4% to 1.2% expressed as a weight by volume of emulsion (w/v), and wherein the percentage of the surfactants is from about 4% to about 8% weight/volume.

9. The emulsion of claim 1, wherein the low HLB non-ionic hydrophilic surfactant is present at a concentration of 2.5% to 4% expressed as a weight by volume of emulsion (w/v).

10. The emulsion of claim 1, wherein the non-ionic lipophilic surfactant is present at a concentration of 0.2% to 1.2% expressed as a weight by volume of emulsion (w/v).

11. The emulsion of claim 1, wherein the low HLB non-ionic hydrophilic surfactant is an ethoxylated fatty acid triester of sorbitan, and wherein the ester of said ethoxylated fatty acid ester is selected from the group consisting of oleate, palmitate, stearate, isostearate, laurate and combinations thereof.

12. The emulsion of claim 1, wherein the non-ionic lipophilic surfactant is a fatty acid ester of sorbitan, and wherein the ester of the fatty acid ester is selected from the group consisting of oleate, palmitate, stearate, isostearate, laurate and combinations thereof.

13. The emulsion of claim 1, wherein the high HLB non-ionic hydrophilic surfactant is an ethoxylated fatty acid monoester of sorbitan, and wherein the ethoxylated monoester of sorbitan is selected from the group consisting of ethoxylated sorbitan monolaurate, ethoxylated sorbitan monopalmitate, ethoxylated sorbitan monostearate, ethoxylated sorbitan monooleate, and combinations thereof.

14. A method for inducing an immunological response in an porcine against a pathogen comprising administering to said animal the emulsion of claim 1.

15. The method of claim 14, wherein the emulsion is administered via the intramuscular (IM), intradermal (ID) or subcutaneous (SC) route, or wherein the administration is done with a needleless injector.

* * * * *